(12) United States Patent
Sanner et al.

(10) Patent No.: US 6,720,427 B2
(45) Date of Patent: Apr. 13, 2004

(54) THIAZOLE DERIVATIVES

(75) Inventors: Mark A. Sanner, Old Saybrook, CT (US); Chris J. Helal, Mystic, CT (US); Christopher B. Cooper, Lawrenceville, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/144,403

(22) Filed: May 13, 2002

(65) Prior Publication Data

US 2003/0078252 A1 Apr. 24, 2003

Related U.S. Application Data

(60) Provisional application No. 60/290,466, filed on May 11, 2001.

(51) Int. Cl.[7] ............... C07D 217/22; C07D 215/16; C07D 277/04; C07D 277/18; C07D 277/38
(52) U.S. Cl. ............... 548/193; 546/142; 546/143; 546/146; 546/148; 546/153; 546/162; 546/167; 546/270.7; 548/190; 548/191; 548/195; 548/196

(56) References Cited

U.S. PATENT DOCUMENTS

| 3,821,239 A | | 6/1974 | Guillot et al. | |
|---|---|---|---|---|
| 6,054,475 A | * | 4/2000 | Martin et al. | 514/432 |
| 6,114,365 A | | 9/2000 | Pevarello et al. | |

FOREIGN PATENT DOCUMENTS

| EP | 0 857 725 | * | 8/1998 |
|---|---|---|---|
| WO | WO 98/28257 | * | 7/1998 |
| WO | WO9924416 | | 5/1999 |
| WO | WO9965884 | | 12/1999 |
| WO | WO0026202 | | 5/2000 |
| WO | WO0026203 | | 5/2000 |

OTHER PUBLICATIONS

Khimicheskii Zhurnal Armenii (2001), vol. 54 No. 1–2, pp. 110–114, CODEN: KZARF3; ISSN: 1561–4190.

Grehn L., A method for nitration of thiazoles, Journal of Heterocyclic Chemistry, vol. 14, No. 5, Aug. 1977, pp. 917–919.

Erlenmeyer H. et al., Uber einige derivate des 2–Aminothiazols, Helvetica Chimica ACTA, vol. 32, No. 1, Feb. 1, 1949, pp. 35–38.

Chemical Abstracts, vol. 47, No. 8, Apr. 25, 1953, abstract No. 38541.

Ganapathi, K., et al., Chemotherapy of malaria. V. Synthesis of 4–(thiazolyamino)quinolines and 4–phenoxyquinolines & Proc. Indian Acad. Sci., vol. 34A, 1951, pp. 178–182.

Nagano, M. et al., "Studies on organic sulfur compounds. IX. The reaction of ethoxycarbonyl isothiocyante with 4,5–substituted 2–aminothiazoles", Chemical and Pharmaceutical Bulletin, vol. 20, No. 12, 1972, pp. 2626–2633.

* cited by examiner

*Primary Examiner*—D. Margaret Seaman
(74) *Attorney, Agent, or Firm*—P. C. Richardson; L. B. Ling; K. L. Konstas

(57) ABSTRACT

The invention provides compounds of formula 1

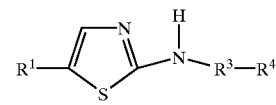

wherein $R^1$, $R^3$, and $R^4$ are as defined, and their pharmaceutically acceptable salts. Compounds of formula 1 are indicated to have activity inhibiting cdk5, cdk2, and GSK-3. Pharmaceutical compositions and methods comprising compounds of formula 1 for treating diseases and conditions comprising abnormal cell growth, such as cancer, and neurodegenerative diseases and conditions and those affected by dopamine neurotransmission are described. Also described are pharmaceutical compositions and methods comprising compounds of formula 1 for treating male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency.

24 Claims, No Drawings

THIAZOLE DERIVATIVES

This application claims priority under 35 U.S.C. 119(e) of U.S. Application No. 60/290,466, filed May 11, 2001.

FIELD OF THE INVENTION

The subject invention relates to thiazole derivatives, pharmaceutical compositions comprising such derivatives and methods of using such derivatives to treat abnormal cell growth and certain diseases and conditions of the central nervous system. The compounds of the present invention act as inhibitors of cyclin-dependent protein kinase enzymes cdk5 (cyclin-dependent protein kinase 5) and cdk2 (cyclin-dependent protein kinase 2). The compounds of the present invention also are inhibitors of the enzyme GSK-3 (glygogen synthase kinase-3) enzyme.

BACKGROUND OF THE INVENTION

The serine/threonine kinase cdk5 along with its cofactor p25 (or the longer cofactor, p35) has been linked to neurodegenerative disorders, and inhibitors of cdk5/p25 (or cdk5/p35) are therefore useful for the treatment of neurodegenerative disorders such as Alzheimer's disease, Parkinson's disease, stroke, or Huntington's disease. Treatment of such neurodegenerative disorders using cdk5 inhibitors is supported by the finding that cdk5 is involved in the phosphorylation of tau protein (*J. Biochem*, 117, 741–749 (1995)). cdk5 also phosphorylates Dopamine and Cyclic AMP-Regulated Phosphorprotein (DARPP-32) at threonine 75 and is thus indicated in having a role in dopaminergic neurotransmission (*Nature*, 402, 669–671 (1999)).

The serine/threonine kinase cdk2 is essential for normal cell cycling and plays a critical role in disorders arising from abnormal cell cycling, a common characteristic of many oncological disorders. Inhibitors of cdk2 are therefore useful for the treatment of various types of cancer and other diseases or conditions related to abnormal cell growth (Meijer, et al., *Properties and Potential-applications of Chemical Inhibitors of Cyclin-dependent Kinsases, Pharmacology & therapeutics*, 82 (2–3), 279–284 (1999); Sausville, et al., *Cyclin-dependent Kinases: Initial Approaches to Exploit a Novel Therapeutic Target, Pharmacology & therapeutics* 82 (2–3) 285–292 (1999)).

GSK-3 is a serine/threonine protein kinase. It is one of several protein kinases which phosphorylate glycogen synthase (Embi, et al., *Eur. J. Biochem.* 107:519–527 (1980); Hemmings, et al., *Eur. J. Biochem.* 119:443–451 (1982)). GSK-3 exists in two isoforms, α and β, in vertebrates, reported as having a monomeric structure of 49 kD and 47 kD respectively. Both isoforms phosphorylate muscle glycogen synthase (Cross, et al., *Biochemical Journal* 303: 21–26 (1994)). The amino acid identity among GSK-3 species homologs has been indicated to be in excess of 98% within the catalytic domain (Plyte, et al., *Biochim. Biophys. Acta* 1114:147–162) (1992)). Due to a remarkably high degree of conservation across the phylogenetic spectrum, a fundamental role of GSK-3 in cellular processes is suggested.

GSK-3 has been implicated in numerous different disease states and conditions. For example, Chen, et al, *Diabetes* 43: 1234–1241 (1994) have suggested that an increase in GSK-3 activity can be important in Type 2 diabetes. Increased GSK-3 expression in diabetic muscle is also though to contribute to the impaired glycogen synthase activity and skeletal muscle insulin resistance present in Type 2 diabetes (Nikoulina, et al., *Diabetes* 49: 263–271 (2000)). Also, a higher activity of a type 1 protein phosphatase measured in immotile sperm was attributed to higher GSK-3 activity and was indicated as responsible for holding the sperm motility in check (Vijayaraghavan, et al. *Biology of Reproduction* 54: 709–718 (1996)). Vijayaraghavan et al. indicate that such results suggest a biochemical basis for the development and regulation of sperm motility and a possible physiological role for a protein phosphatase 1/inhibitor 2/GSK-3 system. GSK-3 activity has also been associated with Alzheimer's disease and mood disorders such as bipolar disorder (WO 97/41854). Among other conditions, GSK-3 has furthermore been implicated in hair loss, schizophrenia, and neurodegeneration, including both chronic neurodegenerative diseases (such as Alzheimer's, supra) and neurotrauma, for example stroke, traumatic brain injury, and spinal cord trauma.

SUMMARY OF THE INVENTION

This invention provides compounds of the formula

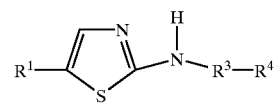

wherein $R^1$ is a straight chain or branched $(C_1-C_8)$alkyl, a straight chain or branched $(C_2-C_8)$alkenyl, a straight chain or branched $(C_2-C_8)$alkynyl, $(C_3-C_8)$cycloalkyl, $(C_4-C_8)$cycloalkenyl, (3–8 membered) heterocycloalkyl, $(C_5-C_{11})$bicycloalkyl, $(C_7-C_{11})$bicycloalkenyl, (5–11 membered) heterobicycloalkyl, $(C_6-C_{14})$ aryl, (5–14 membered) heteroaryl, or ABN-; and wherein $R^1$ is optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

A and B are each independently selected from straight or branched $(C_1-C_8)$alkyl, straight chain or branched $(C_2-C_8)$alkenyl, straight chain or branched $(C_2-C_8)$alkynyl, $(C_3-C_6)$cycloalkyl, $(C_4-C_8)$cycloalkenyl, (3–8 membered) heterocycloalkyl, $(C_5-C_{11})$bicycloalkyl, $(C_7-C_{11})$bicycloalkenyl, and (5–11 membered) heterocycloalkyl; or A and B may be connected to form a 3–8 membered heterocyclic ring optionally containing one or two double bonds and optionally containing one or two further hetero atoms selected independently from O, S, and N; and A and B, or the heterocyclic ring formed thereby, can be optionally independently substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

$R^3$ is —$C(=O)NR^9$—, —$C(=O)O$—, —$C(=O)(CR^{10}R^{11})_n$—, or —$(CR^{10}R^{11})_n$—;

$R^4$ is a straight chain or a branched $(C_1-C_8)$alkyl, a straight chain or a branched $(C_2-C_8)$alkenyl, a straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$) bicycloalkenyl, (5–11 membered) heterobicycloalkyl, ($C_6$–$C_{14}$)aryl, or (5–14 membered) heteroaryl; and wherein $R^4$ is optionally substituted with from one to three substituents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, or $R^7$;

each $R^7$, $R^8$, and $R^9$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^7$, $R^8$, and $R^9$ are each independently optionally substituted with from one to six substituents independently selected from F, Cl, Br, I, $NO_2$, —CN, —$CF_3$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, $OC(=O)R^{10}$, —$OC(=O)OR^{10}$, —$OC(=O)NR^{10}R^{11}$, —$OC(=O)SR^{10}$, —$SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}R^{11}$, and $R^{10}$;

or, when $R^7$ and $R^8$ are as in $NR^7R^8$, they may instead optionally be connected to form with the nitrogen of $NR^7R^8$ to which they are attached a heterocycloalkyl moiety of from three to seven ring members, said heterocycloalkyl moiety optionally comprising one or two further heteroatoms independently selected from N, O, and S;

each $R^{10}$, $R^{11}$, and $R^{12}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{10}$, $R^{11}$, and $R^{12}$ are each independently optionally substituted with from one to six substituents independently selected from F, Cl, Br, I, $NO_2$, —CN, —$CF_3$, —$NR^{13}R^{14}$, —$NR^{13}C(=O)R^{14}$, —$NR^{13}C(=O)OR^{14}$, —$NR^{13}C(=O)NR^{14}R^{15}$, —$NR^{13}S(=O)_2R^{14}$, —$NR^{13}S(=O)_2NR^{14}R^{15}$, —$OR^{13}$, —$OC(=O)R^{13}$, —$OC(=O)OR^{13}$, —$OC(=O)NR^{13}R^{14}$, —$OC(=O)SR^{13}$, —$SR^{13}$, —$S(=O)R^{13}$, —$S(=O)_2R^{13}$, —$S(=O)_2NR^{13}R^{14}$, —$C(=O)R^{13}$, —$C(=O)OR^{13}$, —$C(=O)NR^{13}R^{14}$, and $R^{13}$;

each $R^{13}$, $R^{14}$, and $R^{15}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{13}$, $R^{14}$, and $R^{15}$ are each independently optionally substituted with from one to six substituents independently selected from F, Cl, Br, I, $NO_2$, —CN, —$CF_3$, —$NR^{16}R^{17}$, —$NR^{16}C(=O)R^{17}$, —$NR^{16}C(=O)OR^{17}$, —$NR^{16}C(=O)NR^{17}R^{18}$, —$NR^{16}S(=O)_2R^{17}$, —$NR^{16}S(=O)_2NR^{17}R^{18}$, —$OR^{16}$, —$OC(=O)R^{16}$, —$OC(=O)OR^{16}$, —$OC(=O)NR^{16}R^{17}$, —$OC(=O)SR^{16}$, —$SR^{16}$, —$S(=O)R^{16}$, —$S(=O)_2R^{16}$, —$S(=O)_2NR^{16}R^{17}$, —$C(=O)R^{16}$, —$C(=O)OR^{16}$, —$C(=O)NR^{16}R^{17}$, and $R^{16}$;

each $R^{16}$, $R^{17}$, and $R^{18}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl;

n is 0, 1, 2, or 3;

wherein $R^{10}$ and $R^{11}$ in —$C(=O)(CR^{10}R^{11})_n$— and —$(CR^{10}R^{11})_n$— are for each iteration of n defined independently as recited above;

and pharmaceutically acceptable salts thereof.

Compounds of formula 1 of the invention are inhibitors of serine/threonine kinases, especially cyclin-dependent kinases such as cdk5 and cdk2, and are useful for the treatment of neurodegenerative disorders and other CNS disorders, and of abnormal cell growth, including cancer. The compounds of formula 1 are particularly useful in inhibiting cdk5. Compounds of formula 1 are furthermore also useful as inhibitors of GSK-3.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings, wherein said rings share one or two carbon atoms. For purposes of the present invention, and unless otherwise indicated, bicycloalkyl groups include spiro groups and fused ring groups. Examples of bicycloalkyl groups include, but are not limited to, bicyclo-[3.1.0]-hexyl, norbornyl, spiro[4.5]decyl, spiro [4.4]nonyl, spiro[4.3]octyl, and spiro[4.2]heptyl. "Cycloalkenyl" and "bicycloalkenyl" refer to non-aromatic carbocyclic cycloalkyl and bicycloalkyl moieties as defined above, except comprising one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclobutenyl, and a non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl, and norcamphoryl.

The term "aryl", as used herein, unless otherwise indicated, includes an organic radical derived from an aromatic hydrocarbon by removal of one hydrogen, such as phenyl, naphthyl, indenyl, and fluorenyl.

The terms "heterocyclic", "heterocycloalkyl", and like terms, as used herein, refer to non-aromatic cyclic groups containing one or more heteroatoms, preferably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. In one embodiment, each ring in the heterobicycloalkyl contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

"Heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

In one embodiment, this invention provides compounds of formula 1, wherein $R^1$ is cyclobutyl, optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$. In a further embodiment, $R^1$ is cyclobutyl and $R^3$ is —$C(=O)(CR^{10}R^{11})_n$—.

In another embodiment of the invention, compounds of formula 1 are provided wherein $R^1$ is ABN-.

In another embodiment of the invention, compounds of formula 1 are provided wherein $R^3$ is —$(CR^{10}R^{11})_0$— (in other words, $R^3$ is a bond), and $R^4$ is (3–8 membered) heterocycloalkyl, ($C_6$–$C_{14}$)aryl, or (5–14 membered) heteroaryl, and $R^4$ is optionally substituted with from one to three substituents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, or $R^7$. In a further embodiment of compounds of formula 1 wherein $R^3$ is a bond, $R^4$ is ($C_6$–$C_{14}$)aryl or (5–14 membered) heteroaryl, each optionally substituted. In a more preferred embodiment wherein $R^3$ is a bond, $R^4$ is optionally substituted phenyl or optionally substituted pyridyl. In another preferred embodiment wherein $R^3$ is a bond, $R^4$ is naphthyl, quinolyl, or isoquinolyl, each optionally substituted. In another embodiment wherein $R^3$ is a bond, $R^4$ is napthyl, quinolyl, or isoquinolyl, and is unsubstituted.

In another embodiment of the invention, $R^3$ is a bond and $R^1$ is optionally substituted straight chain or branched ($C_1$–$C_8$)alkyl or optionally substituted straight chain or branched ($C_2$–$C_8$)alkenyl In another embodiment, this invention provides compounds of formula 1, wherein $R^3$ is —$C(=O)NR^9$— or —$C(=O)(CR^{10}R^{11})_n$—. In another embodiment, $R^{10}$ and $R^{11}$ of —$C(=O)(CR^{10}R^{11})_n$— are at each iteration of n both hydrogen. In another embodiment, $R^9$ of —$C(=O)NR^9$— is hydrogen. In another embodiment, and $R^3$ is —$C(=O)$$NR^9$— or —$C(=O)(CR^{10}R^{11})_n$—.

In another embodiment of the invention, a compound of formula 1 is provided wherein $R^1$ is optionally substituted ($C_3$–$C_8$)cycloalkyl or optionally substituted ($C_5$–$C_{11}$) bicycloalkyl. Preferred embodiments are wherein $R^1$ is cyclopropyl, cyclobutyl, cyclopentyl, cyclohexyl, or norbornyl, each optionally substituted as recited above (i.e. optionally with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$). In a more preferred embodiment, $R^1$ is ($C_3$–$C_8$)cycloalkyl or optionally substituted ($C_5$–$C_{11}$) bicycloalkyl, for example cyclopropyl, cyclobutyl, cyclopentyl, cyclohexyl, or norbornyl, and is optionally substituted with from one to three substituents independently selected from F, Cl, Br, I, nitro, cyano, —$CF_3$, —$NR^7R^8$, —$NR^7C(=O)R^8$, —$OR^7$, —$C(=O)OR^7$, —$C(=O)R^7$, and $R^7$. More preferably, $R^1$ is ($C_3$–$C_8$) cycloalkyl or optionally substituted ($C_5$–$C_{11}$) bicycloalkyl, for example cyclopropyl, cyclobutyl, cyclopentyl, cyclohexyl, or norbornyl, and $R^1$ is substituted with —$NR^7C(=O)R^8$, ($C_6$–$C_{14}$)aryl, (3–8 membered) heterocycloalkyl, or (5–14 membered) heteroaryl, and wherein said aryl, heterocycloalkyl, and heteroaryl are each optionally substituted with from one to six substituents independently selected from F, Cl, Br, I, NO$_2$, —CN, —CF$_3$, —NR$^{10}$R$^{11}$, —NR$^{10}$C(=O)R$^{11}$, —NR$^{10}$C(=O)OR$^{11}$, —NR$^{10}$C(=O)NR$^{11}$R$^{12}$, —NR$^{10}$S(=O)$_2$R$^{11}$, —NR$^{10}$S(=O)$_2$NR$^{11}$R$^{12}$, —OR$^{10}$, —OC(=O)R$^{10}$, —OC(=O)R$^{10}$, —OC(=O)NR$^{10}$R$^{11}$, —OC(=O)SR$^{10}$, —SR$^{10}$, —S(=O)R$^{10}$, —S(=O)$_2$R$^{10}$, —S(=O)$_2$NR$^{10}$R$^{11}$, —C(=O)R$^{10}$, —C(=O)OR$^{10}$, —C(=O)NR$^{10}$R$^{11}$, and R$^{10}$. In another embodiment of the invention, R$^1$ is bicyclo[3.1.0]-hexyl and is optionally substituted as recited above (i.e. optionally substituted with from one to six substituents R$^5$ independently selected from F, Cl, Br, I, nitro, cyano, —CF$_3$, —NR$^7$R$^8$, —NR$^7$C(=O)R$^8$, —NR$^7$C(=O)OR$^8$, —NR$^7$C(=O)NR$^8$R$^9$, —NR$^7$S(=O)$_2$R$^8$, —NR$^8$R$^9$, —OR$^7$, —OC(=O)R$^7$, —OC(=O)OR$^7$, —C(=O)OR$^7$, —C(=O)R$^7$, —C(=O)NR$^7$R$^8$, —OC(=O)NR$^7$R$^8$, —OC(=O)SR$^7$, —SR$^7$, —S(=O)R$^7$, —S(=O)$_2$R$^7$, —S(=O)$_2$NR$^7$R$^8$, and R$^7$).

In another embodiment of the invention, a compound of formula 1 is provided wherein R$^1$ is optionally substituted straight chain or branched (C$_1$–C$_8$)alkyl or optionally substituted straight chain or branched (C$_2$–C$_8$)alkenyl.

In another embodiment, this invention provides a compound of formula 1 wherein R$^4$ is (C$_6$–C$_{14}$)aryl or (5–14 membered) heteroaryl, each optionally substituted. In a preferred embodiment, R$^4$ is optionally substituted phenyl or optionally substituted pyridyl. In another preferred embodiment, R$^4$ is naphthyl, quinolyl, or isoquinolyl, each optionally substituted. In another embodiment, R$^4$ is napthyl, quinolyl, or isoquinolyl, and is unsubstituted.

Examples of preferred compounds of formula 1 are:

N-(5-cyclobutyl-thiazol-2-yl)-2-phenyl-acetamide;

N-(5-cyclobutyl-thiazol-2-yl)-isobutyramide;

(5-cyclobutyl-thiazol-2-yl)-carbamic acid phenyl ester;

1-(5-cyclobutyl-thiazol-2-yl)-3-(2,4-dichloro-phenyl)-urea;

1-(5-cyclobutyl-thiazol-2-yl)-3-(2,6-difluoro-phenyl)-urea;

1-(5-cyclobutyl-thiazol-2-yl)-3-(3-trifluoromethyl-phenyl)-urea;

1-(4-chloro-3-trifluoromethyl-phenyl)-3-(5-cyclobutyl-thiazol-2-yl)-urea;

1-(5-cyclobutyl-thiazol-2-yl)-3-(2,4,6-trifluoro-phenyl)-urea;

1-(5-cyclobutyl-thiazol-2-yl)-3-(2,4-difluoro-phenyl)-urea;

1-(5-cyclobutyl-thiazol-2-yl)-3-(2-ethyl-phenyl)-urea;

1-(5-cyclobutyl-thiazol-2-yl)-3-(3-phenoxy-phenyl)-urea;

1-(5-cyclobutyl-thiazol-2-yl)-3-(4-methoxy-phenyl)-urea;

N-(5-cyclobutyl-thiazol-2-yl)-2-(2,4-dichloro-phenyl)-acetamide;

1-(5-cyclobutyl-thiazol-2-yl)-3-phenyl-urea;

1-(4-bromo-3-trifluoromethyl-phenyl)-3-(5-cyclobutyl-thiazol-2-yl)-urea;

1-(5-cyclobutyl-thiazol-2-yl)-3-(1H-indol-5-yl)-urea;

1-(5-cyclobutyl-thiazol-2-yl)-3-(2-methylsulfanyl-phenyl)-urea;

N-(5-cyclobutyl-thiazol-2-yl)-2-(4-methoxy-phenyl)-acetamide;

1-(5-cyclobutyl-thiazol-2-yl)-3-[4-(4-methyl-piperazine-1-sulfonyl)-phenyl]-urea;

1-(5-cyclobutyl-thiazol-2-yl)-3-quinolin-6-yl-urea;

1-(5-cyclobutyl-thiazol-2-yl)-3-(2-methyl-quinolin-6-yl)-urea;

3-{2-[2-(2,4-dichloro-phenyl)-acetylamino]-thiazol-5-yl}-cyclobutanecarboxylic acid butyl ester;

N-(5-cyclobutyl-thiazol-2-yl)-2-pyridin-3-yl-acetamide;

3-{2-[2-(2,4-dichloro-phenyl)-acetylamino]-thiazol-5-yl}-cyclobutanecarboxylic acid;

1-(5-cyclobutyl-thiazol-2-yl)-3-(4-pyridin-3-yl-phenyl)-urea;

1-benzothiazol-5-yl-3-(5-cyclobutyl-thiazol-2-yl)-urea;

N-(5-cyclobutyl-thiazol-2-yl)-2-quinolin-6-yl-acetamide;

1-(3H-benzotriazol-5-yl)-3-(5-cyclobutyl-thiazol-2-yl)-urea;

1-(5-cyclobutyl-thiazol-2-yl)-3-(2-methyl-benzothiazol-5-yl)-urea;

1-biphenyl-3-yl-3-(5-cyclobutyl-thiazol-2-yl)-urea;

1-(3H-benzoimidazol-5-yl)-3-(5-cyclobutyl-thiazol-2-yl)-urea;

1-(5-cyclobutyl-thiazol-2-yl)-3-[4-(2-dimethylamino-ethylamino)-quinolin-6-yl]-urea;

1-(5-cyclobutyl-thiazol-2-yl)-3-[4-(3-hydroxy-propylamino)-quinolin-6-yl]-urea;

(5-cyclobutyl-thiazol-2-yl)-carbamic acid 3-(6-amino-quinolin-4-ylamino)-propyl ester;

N-(5-cyclobutyl-thiazol-2-yl)-2-(2-methyl-benzothiazol-6-yl)-acetamide;

3-hydroxy-pyrrolidine-1-carboxylic acid (5-cyclobutyl-thiazol-2-yl)-amide;

1-(5-cyclobutyl-thiazol-2-yl)-3-[4-(2-hydroxy-cyclohexylamino)-quinolin-6-yl]-urea;

1-(5-cyclobutyl-thiazol-2-yl)-3-quinolin-5-yl-urea;

1-(5-cyclobutyl-thiazol-2-yl)-3-isoquinolin-6-yl-urea;

1-(5-cyclobutyl-thiazol-2-yl)-3-[4-(3-hydroxy-pyrrolidine-1-yl)-quinolin-6-yl]-urea;

1-(5-cyclobutyl-thiazol-2-yl)-3-isoquinolin-5-yl-urea;

2-(1H-benzoimidazol-5-yl)-N-(5-cyclobutyl-thiazol-2-yl)-acetamide;

N-(5-cyclobutyl-thiazol-2-yl)-2-(5,6-dimethyl-benzoimidazol-1-yl)-acetamide;

1-(5-cyclobutyl-thiazol-2-yl)-3-[4-(2-hydroxy-cyclopentylamino)-quinolin-6-yl]-urea;

N-(5-cyclobutyl-thiazol-2-yl)-2-indol-1-yl-acetamide;

1-(3H-benzoimidazol-4-yl)-3-(5-cyclobutyl-thiazol-2-yl)-urea;

N-(5-cyclobutyl-thiazol-2-yl)-2-(1H-indol-3-yl)-acetamide;

N-(5-cyclobutyl-thiazol-2-yl)-2-quinolin-5-yl-acetamide;

1-(5-cyclobutyl-thiazol-2-yl)-3-(1H-indazol-6-yl)-urea;

1-(5-cyclobutyl-thiazol-2-yl)-3-(4-methyl-2-oxo-1,2-dihydro-quinolin-7-yl)-urea;

1-(5-cyclobutyl-thiazol-2-yl)-3-[2-(4-nitro-phenyl)-1H-benzoimidazol-5-yl]-urea;

1-benzo[1,3]dioxol-5-yl-3-(5-cyclobutyl-thiazol-2-yl)-urea;

1-(5-cyclobutyl-thiazol-2-yl)-3-(4-methoxymethyl-2-oxo-2H-chromen-7-yl)-urea;

1-(5-cyclobutyl-thiazol-2-yl)-3-(4-methyl-2-oxo-2H-chromen-7-yl)-urea;

1-(5-cyclobutyl-thiazol-2-yl)-3-(2-oxo-2,3-dihydro-1H-benzoimidazol-5-yl)-urea;

1-(1-acetyl-2,3-dihydro-1H-indol-6-yl)-3-(5-cyclobutyl-thiazol-2-yl)-urea;

1-(5-cyclobutyl-thiazol-2-yl)-3-(4,7-dimethoxy-3H-benzoimidazol-5-yl)-urea;

1-(5-cyclobutyl-thiazol-2-yl)-3-(2-pyridin-2-yl-1H-benzoimidazol-5-yl)-urea;

1-(5-cyclobutyl-thiazol-2-yl)-3-[2-(1,1,2,2,3,3,3-heptafluoro-propyl)-1H-benzoimidazol-5-yl]-urea;

1-(5-cyclobutyl-thiazol-2-yl)-3-(6-fluoro-3-prop-2-ynyl-2-trifluoromethyl-3H-benzoimidazol-5-yl)-urea;

1-(5-cyclobutyl-thiazol-2-yl)-3-(1-ethyl-2-methyl-1H-benzoimidazol-5-yl)-urea;

1-(5-cyclobutyl-thiazol-2-yl)-3-(1H-indol-6-yl)-urea;

1-(5-cyclobutyl-thiazol-2-yl)-3-(2-methyl-1H-benzoimidazol-5-yl)-urea;

5-[3-(5-cyclobutyl-thiazol-2-yl)-ureido]-1H-indole-2-carboxylic acid ethyl ester;

1-benzo[1,2,3]thiadiazol-4-yl-3-(5-cyclobutyl-thiazol-2-yl)-urea;

1-(5-cyclobutyl-thiazol-2-yl)-3-(1,4-dioxo-1,2,3,4-tetrahydro-phthalazin-5-yl)-urea;

1-(5-cyclobutyl-thiazol-2-yl)-3-(1H-indazol-7-yl)-urea;

1-(5-cyclobutyl-thiazol-2-yl)-3-(1H-indol-4-yl)-urea;

1-(5-cyclobutyl-thiazol-2-yl)-3-(2-oxo-2,3-dihydro-1H-benzoimidazol-4-yl)-urea;

1-benzooxazol-4-yl-3-(5-cyclobutyl-thiazol-2-yl)-urea;

N-(5-cyclobutyl-thiazol-2-yl)-2-(2-methyl-3H-benzoimidazol-5-yl)-acetamide;

1-(5-cyclobutyl-thiazol-2-yl)-3-quinolin-8-yl-urea;

1-(5-cyclobutyl-thiazol-2-yl)-3-isoquinolin-8-yl-urea;

1-(3H-benzotriazol-4-yl)-3-(5-cyclobutyl-thiazol-2-yl)-urea;

N-(5-cyclobutyl-thiazol-2-yl)-2-isoquinolin-5-yl-acetamide;

N-(5-cyclobutyl-thiazol-2-yl)-2-quinolin-6-yl-acetamide;

1-(5-cyclobutyl-thiazol-2-yl)-3-isoquinolin-5-yl-urea;

N-[5-(3-acetylamino-cyclobutyl)-thiazol-2-yl]-2-quinolin-6-yl-acetamide;

N-(5-cyclobutyl-thiazol-2-yl)-2-(4-nitro-phenyl)-acetamide;

2-(4-amino-phenyl)-N-(5-cyclobutyl-thiazol-2-yl)-acetamide;

2-(4-acetylamino-phenyl)-N-(5-cyclobutyl-thiazol-2-yl)-acetamide;

N-(5-cyclobutyl-thiazol-2-yl)-2-[4-(2-pyridin-3-yl-acetylamino)-phenyl]-acetamide;

N-(5-cyclobutyl-thiazol-2-yl)-2-[4-(2-morpholin-4-yl-ethylamino)-phenyl]-acetamide;

(5-isopropyl-thiazol-2-yl)-pyridin-2-yl-amine;

(3-chloro-5-trifluoromethyl-pyridin-2-yl)-(5-isopropyl-thiazol-2-yl)-amine;

(5-isopropyl-thiazol-2-yl)-phenyl-amine;

(5-chloro-pyridin-2-yl)-(5-isopropyl-thiazol-2-yl)-amine;

(5-isopropyl-thiazol-2-yl)-(6-methyl-pyridin-2-yl)-amine;

(5-isopropyl-thiazol-2-yl)-(5-methyl-pyridin-2-yl)-amine;

(5-isopropyl-thiazol-2-yl)-(4-methyl-pyridin-2-yl)-amine;

(2-chloro-pyridin-4-yl)-(5-isopropyl-thiazol-2-yl)-amine; and

N-(5-dimethylamino-thiazol-2-yl)-2-phenyl-acetamide;

and pharmaceutically acceptable salts of the foregoing compounds.

Salts of compounds of formula 1 can be obtained by forming salts with any acidic or basic group present on a compound of formula 1. Examples of pharmaceutically acceptable salts of the compounds of formula 1 are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium.

The compounds of formula 1 may have optical centers and therefore may occur in different enantiomeric and other stereoisomeric configurations. The invention includes all enantiomers, diastereomers, and other stereoisomers of such compounds of formula 1, as well as racemic and other mixtures thereof.

The subject invention also includes isotopically-labeled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula 1 of this invention can generally be prepared by carrying out the procedures disclosed in the Schemes and/or in the Examples below, by substituting a readily available isotopically labeled reagent for a non-isotopically labeled reagent.

This invention also provides a pharmaceutical composition for treating a disease or condition comprising abnormal cell growth in a mammal comprising a compound of formula 1 in an amount effective in inhibiting abnormal cell growth, and a pharmaceutically acceptable carrier.

This invention also provides a pharmaceutical composition for treating a disease or condition comprising abnormal cell growth in a mammal comprising a compound of formula 1 in an amount effective to inhibit cdk2 activity, and a pharmaceutically acceptable carrier.

This invention also provides a method for treating a disease or condition comprising abnormal cell growth in a mammal comprising administering to the mammal a compound of formula 1 in an amount effective in inhibiting abnormal cell growth.

This invention also provides a method for treating a diseases or condition comprising abnormal cell growth in a mammal comprising administering to the mammal a compound of formula 1 in an amount effective to inhibit cdk2 activity.

In a pharmaceutical composition or method of this invention for treating a disease or condition comprising abnormal cell growth, the disease or condition comprising abnormal cell growth is in one embodiment cancer. The cancer may be a carcinoma, for example carcinoma of the bladder, breast, colon, kidney, liver, lung, for example small cell lung cancer, esophagus, gall bladder, ovary, pancreas, stomach, cervix, thyroid, prostate, or skin, for example squamous cell carcinoma; a hematopoietic tumor of lymphoid lineage, for example leukemia, acute lymphocytic leukemia, B-cell lymphoma, T-cell lymphoma, Hodgkins lymphoma, non-Hodgkins lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; a tumor of mesenchymal origin, for example fibrosarcoma or rhabdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

In another embodiment, the disease or condition comprising abnormal cell growth is benign. Such diseases and conditions include benign prostate hyperplasia, familial adenomatosis polyposis, neuro-fibromatosis, atherosclerosis, pulmonary fibrosis, arthritis, psoriasis, glomerulonephritis, restenosis, hypertrophic scar formation, inflammatory bowel disease, transplantation rejection, fungal infection, and endotoxic shock.

This invention also provides a pharmaceutical composition for treating a neurodegenerative disease or condition in a mammal comprising a compound of formula 1 in an amount effective in treating said disease or condition, and a pharmaceutically acceptable carrier.

This invention also provides a pharmaceutical composition for treating a neurodegenerative disease or condition in a mammal comprising a compound of formula 1 in an amount effective in inhibiting cdk5 activity, and a pharmaceutically acceptable carrier.

This invention also provides a method for treating a neurodegenerative disease or condition in a mammal comprising administering to the mammal a compound of formula 1 in an amount effective in inhibiting cdk5 activity.

This invention also provides a method for treating a neurodegenerative disease or condition in a mammal comprising administering to the mammal a compound of formula 1 in an amount effective in treating said disease or condition.

In one embodiment of the invention, the neurodegenerative disease or condition which is treated is selected from Huntington's disease, stroke, spinal cord trauma, traumatic brain injury, multiinfarct dementia, epilepsy, amyotrophic lateral sclerosis, pain, viral induced dementia for example AIDS induced dementia, neurodegeneration associated with bacterial infection, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis.

This invention also provides a pharmaceutical composition for treating a disease or condition the treatment of which can be effected or facilitated by altering dopamine mediated neurotransmission in a mammal comprising a compound of formula 1 in an amount effective in treating said disease or condition and a pharmaceutically acceptable carrier.

This invention also provides a pharmaceutical composition for treating a disease or condition the treatment of which can be effected or facilitated by altering dopamine mediated neurotransmission in a mammal comprising a compound of formula 1 in an amount effective to inhibit cdk5 and a pharmaceutically acceptable carrier.

This invention also provides a method for treating a disease or condition the treatment of which can be effected or facilitated by altering dopamine mediated neurotransmission in a mammal comprising administering to the mammal a compound of formula 1 in an amount effective in inhibiting cdk5 activity.

This invention also provides a method for treating a disease or condition the treatment of which can be effected or facilitated by altering dopamine mediated neurotransmission in a mammal comprising administering to the mammal a compound of formula 1 in an amount effective in treating said disease or condition.

In one embodiment of the invention, the disease or condition the treatment of which can be effected or facilitated by altering dopamine mediated neurotransmission is selected from Parkinson's disease; schizophrenia; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; drug addiction, including narcotic (e.g. heroin, opium, and morphine), cocaine and alcohol addiction; drug withdrawal, including narcotic, cocaine and alcohol withdrawal; obsessive compulsive disorder; Tourette's syndrome; depression; a major depressive episode, a manic or mixed mood episode, a hypomanic mood episode, a depressive episode with atypical features or with melancholic features or catatonic features, a mood episode with postpartum onset; post-stroke depression, major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example bipolar I disorder, bipolar II disorder, cyclothymic disorder; anxiety; attention deficit and hyperactivity disorder; and attention deficit disorder.

This invention also provides a method for treating a disease or condition facilitated by cdk5 activity in a mammal which method comprises administering to the mammal a compound of formula 1 in an amount effective in inhibiting cdk5 activity.

We have also found that the compounds of formula 1 have activity in inhibiting GSK-3. The compounds of formula I therefore can be expected to be useful in treating diseases and conditions the treatment of which can be effected or facilitated by inhibition of GSK-3. Diseases and conditions the treatment of which can be effected or facilitated by inhibiting GSK-3 include neurodegenerative diseases and conditions. Neurodegenerative diseases and conditions are discussed above and include, but are not limited to, for example Alzheimer's disease, Parkinson's disease, Huntington's disease, amyotrophic lateral sclerosis, multiple sclerosis, stroke, cerebral ischemia, AIDS-related dementia, neurodegeneration associated with bacterial infection, multiinfarct dementia, traumatic brain injury, and spinal cord trauma. Therefore, compounds of formula 1 are effective in treating neurodegenerative diseases and conditions based on both cdk5 activity and GSK-3 activity.

Other diseases and conditions the treatment of which can be effected or facilitated by inhibiting GSK-3 include psychotic disorders and conditions, for example schizophrenia, schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type. The treatment of such diseases and conditions can also be effected or facilitated by altering dopamine mediated neurotransmission. Therefore, compounds of formula 1 are effective in treating such disorders and conditions based on both cdk5 activity and GSK-3 activity.

Other disorders and conditions the treatment of which can be effected or facilitated by inhibiting GSK-3 include mood disorders and mood episodes, for example a major depressive episode, a manic or mixed mood episode, a hypomanic mood episode, a depressive episode with atypical features or with melancholic features or catatonic features, a mood episode with postpartum onset; post-stroke depression, major depressive disorder, dysthymic disorder, minor depressive disorder, premenstrual dysphoric disorder, postpsychotic depressive disorder of schizophrenia, a major depressive disorder superimposed on a psychotic disorder such as delusional disorder or schizophrenia, a bipolar disorder, for example bipolar I disorder, bipolar II disorder, and cyclothymic disorder. The treatment of such mood disorders and episodes, for example depression, can also be effected or facilitated by altering dopamine mediated neurotransmission. Therefore, compounds of formula 1 are effective in treating certain mood disorders and mood episodes based on both cdk5 activity and GSK-3 activity.

Other disorders and conditions the treatment of which can be effected or facilitated by inhibiting GSK-3 are male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; spinal cord injury; hair loss, hair thinning, and balding; immunodeficiency; and cancer.

Accordingly, the present invention also provides a pharmaceutical composition for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which composition comprises a pharmaceutically acceptable carrier and an amount of a compound of formula 1 effective in treating said disease or condition.

The present invention further provides a pharmaceutical composition for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which composition comprises a pharmaceutically acceptable carrier and an amount of a compound of formula 1 effective in inhibiting GSK-3.

The present invention also provides a method for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which method comprises administering to said mammal an amount of a compound of formula 1 effective in treating said disease or condition.

The present invention also provides a method for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which method comprises administering to said mammal an amount of a compound of formula 1 effective in inhibiting GSK-3.

The present invention further provides a method for inhibiting GSK-3 in a mammal, including a human, which method comprises administering to said mammal an amount of a compound of formula I1 effective in inhibiting GSK-3.

The present invention further provides a pharmaceutical composition for treating in a mammal a disorder selected from Alzheimer's disease, mild cognitive impairment, and age-related cognitive decline comprising a compound of formula 1 and a COX-II inhibitor together in an amount effective in treating said disorder, and a pharmaceutically acceptable carrier.

This invention also provides a method for treating in a mammal a disorder selected from Alzheimer's disease, mild cognitive impairment, and age-related cognitive decline which method comprises administering to said mammal a compound of formula 1 and a COX-II inhibitor, wherein the combined amounts of the compound of formula 1 and the COX-II inhibitor are effective in treating said disorder. The compound of formula 1 and the COX-II inhibitor can be administered to the mammal at the same time and/or at different times. Moreover, they may be administered together in a single pharmaceutical composition or in separate pharmaceutical compositions.

Moreover, a compound of formula 1 of the invention, or a pharmaceutically acceptable salt of a compound of formula 1, can be administered or formulated into a pharmaceutical composition with one or more anti-depressants or anxiolytic compounds for treatment or prevention of depression and/or anxiety.

Accordingly, this invention also provides a pharmaceutical composition for treating depression or anxiety in a mammal comprising a compound of formula 1 and an NK-1 receptor antagonist together in an amount effective in treating depression or anxiety, and a pharmaceutically acceptable carrier.

This invention further provides a method for treating depression or anxiety in a mammal which method comprises administering to said mammal a compound of formula 1 and an NK-1 receptor antagonist, wherein the combined amounts of the compound of formula 1 and the NK-1 receptor antagonist are effective in treating depression or anxiety. The compound of formula 1 and the NK-1 receptor antagonist can be administered to the mammal at the same time and/or at different times. Moreover, they may be administered together in a single pharmaceutical composition or in separate pharmaceutical compositions.

This invention also provides a pharmaceutical composition for treating depression or anxiety in a mammal comprising a compound of formula 1 and a $5HT_{1D}$ receptor antagonist together in an amount effective in treating depression or anxiety, and a pharmaceutically acceptable carrier.

This invention further provides a method for treating depression or anxiety in a mammal which method comprises administering to said mammal a compound of formula 1 and a $5HT_{1D}$ receptor antagonist, wherein the combined amounts of the compound of formula 1 and the $5HT_{1D}$ receptor antagonist are effective in treating depression or anxiety. The compound of formula 1 and the $5HT_{1D}$ receptor antagonist can be administered to the mammal at the same time and/or at different times. Moreover, they may be administered together in a single pharmaceutical composition or in separate pharmaceutical compositions.

This invention also provides a pharmaceutical composition for treating depression or anxiety in a mammal comprising a compound of formula 1 and a SSRI together in an amount effective in treating depression or anxiety, and a pharmaceutically acceptable carrier.

This invention further provides a method for treating depression or anxiety in a mammal which method comprises administering to said mammal a compound of formula 1 and a SSRI, wherein the combined amounts of the compound of formula 1 and the SSRI are effective in treating depression or anxiety. The compound of formula 1 and the SSRI can be administered to the mammal at the same time and/or at different times. Moreover, they may be administered together in a single pharmaceutical composition or in separate pharmaceutical compositions.

This invention also provides a pharmaceutical composition for treating schizophrenia in a mammal comprising a compound of formula 1 and as antipsychotic selected from ziprasidone, olanzapine, risperidone, L-745870, sonepiprazole, RP 62203, NGD 941, balaperidone, flesinoxan, and gepirone, together in an amount effective in treating schizophrenia, and a pharmaceutically acceptable carrier.

This invention further provides a method for treating schizophrenia in a mammal which method comprises administering to said mammal a compound of formula 1 and an antipsychotic selected from ziprasidone, olanzapine, risperidone, L-745870, sonepiprazole, RP 62203, NGD 941, balaperidone, flesinoxan, and gepirone, wherein the combined amounts of the cdk5 inhibitor and the antipsychotic are effective in treating schizophrenia. The compound of formula 1 and the antipsychotic can be administered to the mammal at the same time and/or at different times. Moreover, they may be administered together in a single pharmaceutical composition or in separate pharmaceutical compositions.

This invention also provides a pharmaceutical composition for treating a disorder selected from Alzheimer's disease, mild cognitive impairment, and age-related cognitive decline in a mammal comprising a compound of formula 1 and an acetylcholinesterase inhibitor together in an amount effective in treating said disorder, and a pharmaceutically acceptable carrier.

This invention further provides a method for treating in a mammal a disorder selected from Alzheimer's disease, mild cognitive impairment, and age-related cognitive decline, which method comprises administering to said mammal a compound of formula 1 and an acetylcholinesterase inhibitor, wherein the combined amounts of the compound of formula 1 and the acetylcholinesterase inhibitor are effective in treating said disorder. The compound of formula 1 and the acetylcholinesterase inhibitor can be administered to the mammal at the same time and/or at different times.

This invention also provides a pharmaceutical composition for treating a disease or condition selected from stroke, spinal cord trauma, traumatic brain injury, multiinfarct dementia, epilepsy, pain, Alzheimer's disease, and senile dementia comprising a compound of formula 1 and TPA (tissue plasminogen activator, for example ACTIVASE) together in an amount effective in treating said disorder, and a pharmaceutically acceptable carrier.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a compound of formula 1 and TPA, wherein the combined amounts of the compound of formula 1 and the TPA are effective in treating said disease or condition. The compound of formula 1 and the TPA can be administered to the mammal at the same time and/or at different times. Moreover, they may be administered together in a single pharmaceutical composition or in separate pharmaceutical compositions.

This invention also provides a pharmaceutical composition for treating a disease or condition selected from stroke, spinal cord trauma, traumatic brain injury, multiinfarct dementia, epilepsy, pain, Alzheimer's disease, and senile dementia in a mammal comprising a compound of formula 1 and NIF (neutrophil inhibitory factor) together in an amount effective in treating said disorder, and a pharmaceutically acceptable carrier.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a compound of formula 1 and NIF, wherein the combined amounts of the compound of formula 1 and the NIF are effective in treating said disease or condition. The compound of formula 1 and the NIF can be administered to the mammal at the same time and/or at different times. Moreover, they may be administered together in a single pharmaceutical composition or in separate pharmaceutical compositions.

This invention also provides a pharmaceutical composition for treating a disease or condition selected from Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis in a mammal comprising a compound of formula 1 and an NMDA receptor antagonist together in an amount effective in treating said disorder, and a pharmaceutically acceptable carrier.

This invention further provides a method for treating in a mammal a disease or condition selected from Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis, which method comprises administering to said mammal a compound of formula 1 and an NMDA receptor antagonist, wherein the combined amounts of the compound of formula 1 and the NMDA receptor antagonist are effective in treating said disease or condition. The compound of formula 1 and the NMDA receptor antagonist can be administered to the mammal at the same time and/or at different times. Moreover, they may be administered together in a single pharmaceutical composition or in separate pharmaceutical compositions.

This invention also provides a pharmaceutical composition for treating a disease or condition selected from stroke, spinal cord trauma, traumatic brain injury, multiinfarct dementia, epilepsy, pain, Alzheimer's disease, and senile dementia in a mammal comprising a compound of formula 1 and a potassium channel modulator together in an amount effective in treating said disorder, and a pharmaceutically acceptable carrier.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a compound of formula 1 and a potassium channel modulator, wherein the combined amounts of the compound of formula 1 and the potassium channel modulator are effective in treating said disease or condition. The compound of formula 1 and the potassium channel modulator can be administered to the mammal at the same time and/or at different times. Moreover, they may be administered together in a single pharmaceutical composition or in separate pharmaceutical compositions.

The terms "treatment", "treating", and the like, refers to reversing, alleviating, or inhibiting the progress of the disease or condition to which such term applies, or one or more symptoms of such disease or condition. As used herein, these terms also encompass, depending on the condition of the patient, preventing the onset of a disease or condition, or of symptoms associated with a disease or condition, including reducing the severity of a disease or condition or symptoms associated therewith prior to afflication with said disease or condition. Such prevention or reduction prior to affliction refers to administration of the compound of the invention to a subject that is not at the time of administration afflicted with the disease or condition. "Preventing" also encompasses preventing the recurrence of a disease or condition or of symptoms associated therewith.

"Mammal", as used herein, and unless otherwise indicated, means any mammal. The term "mammal" includes, for example and without limitation, dogs, cats, and humans.

"Abnormal cell growth", as used herein, refers to cell growth, either malignant (e.g. as in cancer) or benign, that is independent of normal regulatory mechanisms (e.g., loss of contact inhibition). Examples of benign proliferative diseases are psoriasis, benign prostatic hypertrophy, human papilloma virus (HPV), and restinosis.

"Neurodegenerative diseases and conditions", as used herein, refers to diseases and conditions having associated therewith degeneration of neurons. Conditions and diseases that are neurodegenerative in nature are generally known to those of ordinary skill in the art.

References herein to diseases and conditions "the treatment of which can be effected or facilitated by altering dopamine mediated neurotransmission" mean a disease or condition that is caused at least in part by dopamine neurotransmission, or a disease or condition that result in abnormal dopamine neurotransmission, thus contributing to symptoms or manifestations of the disease or condition.

References herein to diseases and conditions "the treatment of which can be effected or faciliatated by decreasing cdk5 activity" mean a disease or condition that is caused at least in part by cdk5 activity, or a disease or condition that results in abnormal cdk5 activity that contributes to symptoms or manifestations of the disease or condition.

An "amount effective to inhibit cdk5 activity" as used herein refers to an amount of a compound sufficient to bind to the enzyme cdk5 with the effect of decreasing cdk5 activity.

An "amount effective to inhibit cdk2 activity" as used herein refers to an amount of a compound sufficient to bind to the enzyme cdk2 with the effect of decreasing cdk2 activity.

DETAILED DESCRIPTION OF THE INVENTION

Compounds of the formula 1, above, and their pharmaceutically acceptable salts, can be prepared according to the following reaction Schemes and discussion. Unless otherwise indicated $R^1$, $R^3$, and $R^4$ are as defined above. Isolation and purification of the products is accomplished by standard procedures which are known to a chemist of ordinary skill.

As used herein, the expression "reaction inert solvent" refers to a solvent system in which the components do not interact with starting materials, reagents, or intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991.

Scheme 1 illustrates methods suitable for preparing compounds of formula 1 wherein $R^3$ is a bond or $C(=O)$. Treatment of an aldehyde 2 with 5,5-dibromobarbituric acid in an inert organic solvent such as diethyl ether at about 23° C. for approximately 13 hours affords α-bromoaldehyde 3 which can then be reacted with thiourea C. If $R^3$ is a bond and $R^4$ is aryl, heteroaryl, heterocyclic, alkyl, or cycloalkyl, then compounds of formula 1 are obtained. If $R^3$ is a bond and R⁴ is H, then aminothiazoles of formula 4 are obtained. These aminothiazoles (4) can then be reacted with an acid chloride ClC(=O)(CR¹⁰R¹¹)ₙR⁴, acid anhydride (R⁴(CR¹⁰R¹¹)ₙC(=O))₂O, or an activated carboxylic acid derivative XC(=O)(CR¹⁰R¹¹)ₙR⁴, wherein the activated carboxylic acid derivative is prepared from the carboxylic acid HOC(=O)(CR¹⁰R¹¹)ₙR⁴ and known activating reagents such as dicyclohexyl carbodiimide, 1-(3-dimethylaminopropyl)-3-ethylcarbodiimide hydrochloride, carbonyl diimidazole, 1-propanephosphonic acid cyclic anhyrdide, alkyl or aryl chloroformate, bis(2-oxo-3-oxazolidinyl)phosphinic chloride, benzotriazol-1-yloxy-tris(dimethylamino)phosphonium hexafluorophosphate, or any other such standard literature reagents in the presence of a base, such as triethylamine, diisopropylethylamine, pyridine, or 2,6-lutidine, wherein, 1-propanephosphonic acid cyclic anhyrdide and triethylamine are a preferred combination, from about −78° C. to about 40° C., to afford 1 where R³ is C(=O)(CR¹⁰R¹¹)ₙ and R⁴ is as defined above. Alternatively, 2-aminothiazole 4 can be treated with a base, such as triethylamine, diisopropylethylamine, pyridine, or 2,6-lutidine, and an alkyl or aryl chloroformate, where diisopropylethylamine and phenyl chloroformate are a preferred combination, from about −78° C. to about 40° C. where about −78° C. to about −40° C. are preferred, to afford 1 where R³ is C(=O)O and R⁴ is phenyl. Subsequent treatment of phenyl carbamate 1 with a primary or secondary amine in a solvent such as dioxane, dimethylformamide, or acetonitrile, where dioxane is preferred, at a temperature between about 50° C. and about 110° C., where about 100° C. is preferred, affords the corresponding urea product 1 where R³ is C(=O)NR⁹.

Scheme 2 illustrates an alternative method for preparing compounds of formula 1. A solution of 2-aminothiazole in tetrahydrofuran at about −78° C. is treated with 2 equivalents of n-butyllithium, is stirred approximately 1 hour, 2 equivalents of chlorotrimethylsilane are added dropwise, then the solution is warmed to about −10° C. The solution is cooled back to about −78° C., 1 equivalent of n-butyllithium is added dropwise and after approximately 10 minutes a solution of a ketone or aldehyde in tetrahydrofuran is added. Following aqueous work-up and silica gel chromatography, aminothiazoles of formula 5 are obtained where A and B are defined as above. Dissolution of 5 in trifluoroacetic acid followed by treatment with either triethylsilane or a noble metal catalyst, such as palladium hydroxide on carbon, and hydrogen gas (3 atmospheres), leads to hydrogenolysis of the hydroxyl. The aminothiazoles (4) thus obtained can be treated with a carboxylic acid (HO(=O)C(CR¹⁰R¹¹)ₙR⁴), propanephosphonic acid cyclic anhydride, and triethylamine in a solvent such as ethyl acetate or dichloromethane to afford compounds of formula 1. Alternatively, 2-aminothiazole 4 can be treated with a base, such as triethylamine, diisopropylethylamine, pyridine, or 2,6-lutidine, and an alkyl or aryl chloroformate, where diisopropylethylamine and phenyl chloroformate are a preferred combination, from about −78° C. to about 40° C., where about −78° C. to about −40° C. are preferred, to afford 1 where R³ is C(=O)O and R⁴ is phenyl. Subsequent treatment of phenyl carbamate 1 with a primary or secondary amine in a solvent such as dioxane, dimethylformamide, or acetonitrile, where dioxane is preferred, at a temperature between about 50° C. and about 110° C., where about 100° C. is preferred, affords the corresponding urea product 1 where R³ is C(=O)NR⁹.

Scheme 3 depicts a method for preparing compounds of formula 1 wherein R¹ is ABN-. An aqueous solution consisting of 5-bromo-2-aminothiazole (6) and 20% tetrafluoroboric acid are added to an aqueous slurry of copper powder and sodium nitrite at about 0° C., followed by warming to about 23° C. Standard work-up and purification by radial chromatography afford 5-bromo-2-nitrothiazole 7. Treatment of 7 with triethylamine and ABNH hydrochloride in dimethylsulfoxide at about 60° C. affords 8. Dissolution of 8 in a solvent such as ethyl acetate and treatment with palladium on carbon and hydrogen gas (3 atmospheres) affords aminothiazole 4. The aminothiazoles thus obtained can be treated with a carboxylic acid (HO(=O)C(CR¹⁰R¹¹)ₙR⁴), propanephosphonic acid cyclic anhydride, and triethylamine in a solvent such as ethyl acetate or dichloromethane to afford compounds of formula 1.

Scheme 4 depicts a method for preparing compounds of formula 1 wherein R¹ is nitrogen-substituted cycloalkyl. A dry solution of cyclobutanone-3-carboxylic acid 9 in tetrahydrofuran is treated with diphenylphosphoryl azide and triethylamine at about 23° C. and is warmed at about 60° C. After nitrogen evolution has ceased, benzyl alcohol is added to provide 10. A solution of 2-aminothiazole in tetrahydrofuran at about −78° C. is treated with 2 equivalents of n-butyllithium, is stirred approximately 1 hour, 2 equivalents of chlorotrimethylsilane are added dropwise, then the solution is warmed to about −10° C. The solution is cooled back to about −78° C., 1 equivalent of n-butyllithium is added dropwise and after approximately 10 minutes a solution of ketone 10 in tetrahydrofuran is added. Following aqueous work-up and silica gel chromatography, aminothiazole of formula 5 is obtained. Treatment of 5 in methylene chloride—trifluoroacetic acid with triethylsilane yields 4. Removal of the benzyloxycarbonyl protecting group with methanesulfonic acid (8 equiv.) in trifluoroacetic acid followed by selective acylation of the cycloalkyl amine with an acid anhydride R⁸C(=O)OC(=O)R⁸ and triethylamine in methylene chloride gives 4. Acylation of the aminothiazole nitrogen can be accomplished by mixing a carboxylic acid (HO(=O)C(CR¹⁰R¹¹)ₙR⁴), propanephosphonic acid cyclic anhydride, and triethylamine in a solvent such as ethyl acetate or dichloromethane to afford compounds of formula 1.

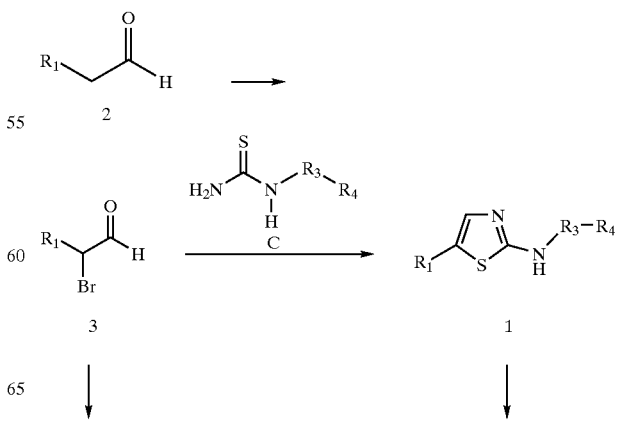

Scheme 1

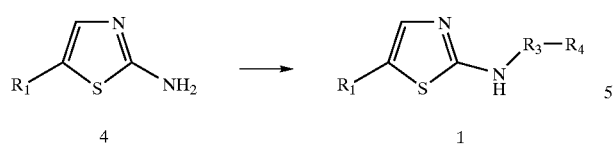
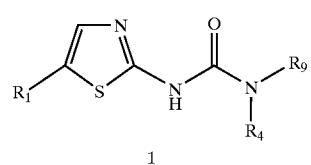
Scheme 3
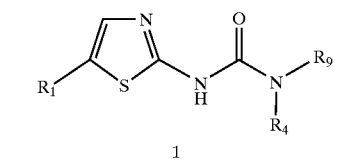
Scheme 2
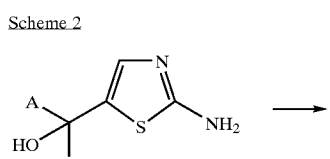
Scheme 4
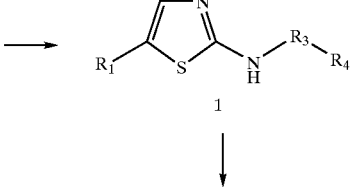
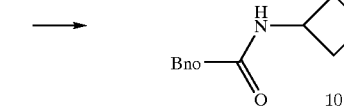

Pharmaceutically acceptable salts of a compound of formula 1 can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula 1 or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula 1 or a pharmaceutically acceptable salt thereof can be administered orally, transdermally (e.g., through the use of a patch), parenterally (e.g. intravenously), rectally, or topically. In general, the daily dosage for treating a neurodegenerative disease or condition or the disease or condition the treatment of which can be effected or facilitated by altering dopamine mediated neurotransmission will generally range from about 0.0001 to about 10.0 mg/kg body weight of the patient to be treated. The daily dosage for treating cancer or disease or condition involving abnormal cell growth of a benign nature will also generally range from about 0.0001 to about 500 mg/kg body weight of the patient to be treated. As an example, a compound of the formula 1 or a pharmaceutically acceptable salt thereof can be administered for treatment of a neurodegenerative disorder to an adult human of average weight (about 70 kg) in a dose ranging from about 0.01 mg up to about 1000 mg per day, preferably from about 0.1 to about 500 mg per day, in single or divided (i.e., multiple) portions. The daily dosage for treating diabetes, sperm motility, hair loss, or any other disease or condition that can be treated by inhibiting GSK-3 will generally range from about 0.0001 to about 10.0 mg/kg body weight of the patient to be treated. Variations based on the aforementioned dosage ranges may be made by a physician of ordinary skill taking into account known considerations such as the weight, age, and condition of the person being treated, the severity of the affliction, and the particular route of administration chosen.

The compounds of formula 1 and their pharmaceutically acceptable salts can furthermore also be administered or formulated into a pharmaceutical composition with an amount of one or more substances selected from anti-angiogenesis agents, signal transduction inhibitors, and anti-proliferative agents, which amounts are together effective in inhibiting abnormal cell growth.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of formula 1 in the methods and pharmaceutical compositions described herein for treatment of abnormal cell growth, including cancer. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

- 3-[[4-(4-fluoro-phenoxy)-benzenesulfonyl]-(1-hydroxycarbamoyl-cyclopentyl)-amino]-propionic acid;
- 3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

The effective amount of a COX-II inhibitor in combination with a cdk5 inhibitor, for example a compound of formula 1, can generally be determined by a person of ordinary skill. A proposed daily effective dose range for a COX-II inhibitor in combination with a compound of formula 1 is from about 0.1 to about 25 mg/kg body weight. The effective daily amount of the compound of formula 1 generally will be between about 0.0001 to about 10 mg/kg body weight. In some instances the amount of COX-II inhibitor and/or compound of formula 1 in the combination may be less than would be required on an individual basis to achieve the same desired effect in inhibiting abnormal cell growth.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA). Such combinations are useful for treating and preventing abnormal cell growth, including cancer, as described herein.

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can also be combined with a compound of formula 1, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substances described in the aforementioned PCT applications, U.S. patents, and U.S. provisional applications, as well as other compounds and substances that inhibit the erbB2 receptor, can be used with a compound of formula 1, in accordance with the present invention.

A compound of formula 1, can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as farnesyl protein transferase inhibitors. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The compounds of formula 1 can also be administered in a method for inhibiting abnormal cell growth in a mammal in combination with radiation therapy. Techniques for administering radiation therapy are known in the art, and these techniques can be used in the combination therapy described herein. The administration of the compound of the invention in this combination therapy can be determined as described herein.

Cdk5 inhibitors, such as compounds of formula 1, can also be administered in combination with a COX-II inhibitor for treating Alzheimer's disease, mild cognitive impairment, or age-related cognitive decline. Specific examples of COX-II inhibitors useful in this aspect of the invention are provided above, wherein use of a COX-II inhibitor in combination with a compound of formula 1 for treatment of abnormal cell growth is described. The effective amount of a COX-II inhibitor in combination with a cdk5 inhibitor, for example a compound of formula 1, can generally be determined by a person of ordinary skill. A proposed effective daily dose range for a COX-II inhibitor in combination with a compound of formula 1 is from about 0.1 to about 25 mg/kg body weight. The daily effective amount of the compound of formula 1 generally will be between about 0.0001 to about 10 mg/kg body weight. In some instances the amount of COX-II inhibitor and/or the amount of compound of formula 1 in the combination may be less than would be required on an individual basis to achieve the same desired effect in treating Alzheimer's disease, mild cognitive impairment, or age-related cognitive decline.

Cdk5 inhibitors, such as compounds of formula 1, can also be administered in combination with an NK-1 receptor antagonist for treatment of depression or anxiety. An NK-1 receptor antagonist, as recited herein, is a substance that is able to antagonize NK-1 receptors, thereby inhibiting tachykinin-mediated responses, such as responses mediated by substance P. Various NK-1 receptor antagonists are known in the art, and any such NK-1 receptor antagonist can be utilized in the present invention as described above in combination with a cdk5 inhibitor, for example a compound of formula 1. NK-1 receptor antagonists are described in, for example, U.S. Pat. No. 5,716,965 (issued Feb. 10, 1998); U.S. Pat. No. 5,852,038 (issued Dec. 22, 1998); WO 90/05729 (International Publication Date May 31, 1990); U.S. Pat. No. 5,807,867 (issued Sep. 15, 1998); U.S. Pat. No. 5,886,009 (issued Mar. 23, 1999); U.S. Pat. No. 5,939,433 (issued Aug. 17, 1999); U.S. Pat. No. 5,773,450 (issued Jun. 30, 1998); U.S. Pat. No. 5,744,480 (issued Apr. 28, 1998); U.S. Pat. No. 5,232,929 (issued Aug. 3, 1993); U.S. Pat. No. 5,332,817 (issued Jul. 26, 1994); U.S. Pat. No. 5,122,525 (issued Jun. 16, 1992), U.S. Pat. No. 5,843,966 (issued Dec. 1, 1998); U.S. Pat. No. 5,703,240 (issued Dec. 30, 1997); U.S. Pat. No. 5,719,147 (issued Feb. 17, 1998); and U.S. Pat. No. 5,637,699 (issued Jun. 10, 1997). Each of the foregoing U.S. patents and the foregoing published PCT International Application are incorporated in their entireties herein by reference. The compounds described in said references having NK-1 receptor antagonizing activity can be used in the present invention. However, other NK-1 receptor antagonists can also be used in this invention.

The effective amount of an NK-1 receptor antagonist in combination with a compound of formula 1 can generally be determined by a person of ordinary skill. A proposed effective daily dose range for an NK-1 receptor antagonist in combination with a compound of formula 1 is from about 0.07 to about 21 mg/kg body weight. The effective amount of the compound of formula 1 generally will be between about 0.0001 to about 10 mg/kg body weight. In some instances the amount of NK-1 receptor antagonist and/or the amount of compound of formula 1 in the combination may be less than would be required on an individual basis to achieve the same desired effect in treating depression or anxiety.

The subject invention also provides combining a compound of formula 1 with a $5HT_{1D}$ receptor antagonist for treatment of depression or anxiety. A $5HT_{1D}$ receptor antagonist, as recited herein, is a substance that antagonizes the $5HT_{1D}$ subtype of serotonin receptor. Any such substance can be used in the present invention as described above in combination with a compound of formula 1. Substances having $5HT_{1D}$ receptor antagonizing activity can be determined by those of ordinary skill in the art. For example, $5HT_{1D}$ receptor antagonists are described in WO 98/14433 (International Publication Date Apr. 9, 1998); WO 97/36867 (International Publication Date Oct. 9, 1997); WO 94/21619 (International Publication Date Sep. 29, 1994); U.S. Pat. No. 5,510,350 (issued Apr. 23, 1996); U.S. Pat. No. 5,358,948 (issued Oct. 25, 1994); and GB 2276162 A (published Sep. 21, 1994). These $5HT_{1D}$ receptor antagonists, as well as others, can be used in the present invention. The aforementioned published patent applications and patents are incorporated herein by reference in their entireties.

The effective amount of a $5HT_{1D}$ receptor antagonist in combination with a cdk5 inhibitor, for example a compound of formula 1, can generally be determined by a person of ordinary skill. A proposed effective daily dose range for a $5HT_{1D}$ receptor antagonist in combination with a compound of formula 1 is from about 0.01 to about 40 mg/kg body weight. The effective daily amount of the compound of formula 1 generally will be between about 0.0001 to about 10 mg/kg body weight. In some instances the amount of $5HT_{1D}$ receptor antagonist and/or the amount of compound of formula 1 in the combination may be less than would be required on an individual basis to achieve the same desired effect in treating depression or anxiety.

This invention also provides a pharmaceutical composition and method for treating depression or anxiety in a mammal comprising a compound of formula 1 and a SSRI. Examples of SSRIs that can be combined in a method or pharmaceutical composition with cdk5 inhibitors, for example compounds of formula 1 and their pharmaceutically acceptable salts include, but are not limited to, fluoxetine, paroxetine, sertraline, and fluvoxamine. Other SSRIs may be combined or administered in combination with a compound of formula 1 or a pharmaceutically acceptable salt thereof. Other antidepressants and/or anxiolytic agents with which a compound of formula 1 may be combined or administered include WELLBUTRIN, SERZONE and EFFEXOR.

The effective amount of a SSRI in combination with a compound of formula 1 can generally be determined by a person of ordinary skill. A proposed effective daily dose range for a SSRI in combination with a compound of formula 1 is from about 0.01 to about 500 mg/kg body weight. The effective daily amount of the compound of formula 1 generally will be between about 0.0001 to about 10 mg/kg body weight. In some instances the amount of SSRI and/or the amount of compound of formula 1 in the combination may be less than would be required on an individual basis to achieve the same desired effect in treating depression or anxiety.

A cdk5 inhibitor, for example a compound of formula 1, or a pharmaceutically acceptable salt thereof, can also be combined with one or more antipsychotic agents, for example a dopaminergic agent, for the treatment of diseases or conditions the treatment of which can be effected or facilitated by altering dopamine neurotransmission, such as schizophrenia. Examples of antipsychotics with which a compound of the invention can be combined include ziprasidone (5-(2-(4-(1,2-benzisothiazol-3-yl)-1-piperazinyl) ethyl)-6-chloro-1,3-dihydro-2H-indol-2-one; U.S. Pat. Nos. 4,831,031 and 5,312,925); olanzapine (2-methyl-4-(4-methyl-1-piperazinyl-10H-thieno (2,3b) (1,5) benzodiazepine; U.S Pat. Nos. 4,115,574 and 5,229,382); risperidone (3-[2-[4-(6-fluoro-1,2-benzisoxazol-3-yl)-1-piperidinyl]ethyl]6,7,8,9-tetrahydro-2-methyl-4H-pyrido[1,2-a]pyrimidin-4-one; U.S. Pat. No. 4,804,663); L-745870 (3-(4-(4-chlorophenyl)piperazin-1-yl)methyl-1H-pyrrolo(2,3-b)pyridine; U.S. Pat. No. 5,432,177); sonepiprazole (S-4-(4-(2-(isochroman-1-yl)ethyl)piperazin-1-yl) benzenesulfonamide; U.S. Pat. No. 5,877,317); RP 62203 (fananserin; 2-(3-(4-(4-fluorophenyl)-1-piperazinyl)propyl) naphtho(1,8-c,d)isothiazole-1,1-dioxide; U.S. Pat. No. 5,021,420); NGD 941 (U.S. Pat. Nos. 5,633,376 and 5,428,165); balaperidone ((1α,5α,6α)-3-(2-(6-(4-fluorophenyl)-3-azabicyclo(3.2.0)hept-3-yl)ethyl)-2,4(1H,3H)-quinazolinedione; U.S. Pat. No. 5,475,105); flesinoxan ((+)-4-fluoro-N-[2-[4-5-(2-hydroxymethyl-1,4-benzodioxanyl)]-1-piperazinyl]ethyl]benzamide; U.S. Pat. No. 4,833,142); and gepirone (4,4-dimethyl-1-(4-(4-(2-pyrimidinyl)-1-piperazinyl)butyl)-2,6-piperidinedione; U.S. Pat. No. 4,423,049). The patents recited above in this paragraph are each incorporated herein by reference in their entireties. The effective daily amount of the compound of formula 1 generally will be between about 0.0001 to about 10 mg/kg body weight. The amount of any of the aforementioned antipsychotic agents contemplated for use in combination with a compound of formula 1 is generally the amount known in the art to be useful for treating psychotic conditions. However, in some instances, the amount of the antipsychotic and/or the amount of compound of formula 1 in the combination may be less than would be required on an individual basis to achieve the same desired effect in treating depression or anxiety. It is furthermore to be understood that the present invention also encompasses combining a compound of formula 1 with antipsychotic or dopaminergic other than those in the aforementioned list.

A proposed amount for sonepiprazole in the above-described combination with a compound of formula 1 is from about 0.005 to about 50 mg/kg body weight of the patient per day. A proposed amount of RP 62203 in such combination is from about 0.20 to about 6 mg/kg body weight of the patient per day. A proposed amount of NGD 941 in such combination is from about 0.1 to about 140 mg/kg of body weight per day. A proposed amount of balaperidone in such combination is from about 1 to about 100 mg/kg body weight per day. A proposed amount of flesinoxan in such combination is from about 0.02 to about 1.6 mg/kg body weight per day. A proposed amount for gepirone in such combination is from about 0.01 to about 2 mg/kg body weight per day. A proposed amount of L-745870 in such combination is from about 0.01 to about 250 mg/kg body weight per day, preferably from about 0.05 to about 100 mg/kg body weight per day. A proposed amount of risperidone in such combination is from about 0.05 to about 50 mg/kg body weight per day. A proposed amount of olanzapine in such combination is from about 0.0005 to about 0.6 mg/kg body weight per day. A proposed amount of ziprasidone in such combination is from about 0.05 to about 10 mg/kg body weight per day. In some instances for each of the aforementioned combinations, however, the amount of each specific ingredient in the combination may be less than would be required on an individual basis to achieve the same desired effect in treating a psychotic condition.

This invention also provides a pharmaceutical composition and method for treating Alzheimer's disease, mild cognitive impairment, or age-related cognitive decline comprising a compound of formula 1 and an acetylcholinesterase inhibitor. Acetylcholinesterase inhibitors are known in the art, and any such acetylcholinesterase inhibitor can be used in the above-described pharmaceutical composition or method. Examples of acetylcholinesterase inhibitors that can be used in this invention are ARICEPT (donepezil; U.S. Pat. No. 4,895,841); EXELON (rivastigmine ((S)-[N-ethyl-3-[1-(dimethylamino)ethyl]phenyl carbamate); U.S. Pat. Nos. 5,603,176 and 4,948,807); metrifonate ((2,2,2-trichloro-1-hydroxyethyl)phosphonic acid dimethyl ester; U.S. Pat. Nos. 2,701,225 and 4,950,658); galantamine (U.S. Pat. No. 4,663,318); physostigmine (Forest, USA); tacrine (1,2,3,4-tetrahydro-9-acridinamine; U.S. Pat. No. 4,816,456); huperzine A (5R-(5α,9β,11E))-5-amino-11-ethylidene-5,6,9,10-tetrahydro-7-methyl-5,9-methaneocycloocta(b) pyridin-2-(1 H)-one); and icopezil (5,7-dihydro-3-(2-(1-(phenylmethyl)-4-piperidinyl)ethyl)-6H-pyrrolo(3,2-f)-1,2-benzisoxazol-6-one; U.S. Pat. No. 5,750,542 and WO 92/17475). The patents and patent applications recited above in this paragraph are herein incorporated by reference in their entireties.

The effective amount of an acetylcholinesterase inhibitor in combination with a compound of formula 1 can generally be determined by a person of ordinary skill. A proposed effective daily dose range for an acetylcholinesterase inhibitor in combination with a compound of formula 1 is from about 0.01 to about 10 mg/kg body weight. The effective daily amount of the compound of formula 1 generally will be between about 0.0001 to about 10 mg/kg body weight. In some instances the amount of acetylcholinesterase inhibitor and/or the amount of compound of formula 1 in the combination may be less than would be required on an individual basis to achieve the same desired effect in treating Alzheimer's disease, mild cognitive impairment, or age-related cognitive decline.

The present invention also provides for combining a compound of formula 1 with neuroprotectants, for example NMDA receptor antagonists, for treatment of Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinence, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progressive supranuclear palsy, lower lateral sclerosis, or subacute sclerosing panencephalistis. Examples of NMDA receptor antagonists that can be used in the present invention include (1S,2S)-1-(4-hydroxyphenyl)-2-(4-hydroxy-4-phenylpiperidin-1-yl)-1-propanol (U.S. Pat. No. 5,272,160), eliprodil (U.S. Pat. No. 4,690,931), and gavestenel (U.S. Pat. No. 5,373,018). Other NMDA receptor antagonists, which can also be used in the present invention, are described in U.S. Pat. Nos. 5,373,018; 4,690,931; 5,272,160; 5,185,343; 5,356,905; 5,744,483; WO 97/23216; WO 97/23215; WO 97/23214; WO 96/37222; WO 96/06081; WO 97/23458; WO 97/32581; WO 98/18793; WO 97/23202; and U.S. Ser. No. 08/292,651 (filed Aug. 18, 1994). The aforementioned patents and patent applications are each hereby incorporated by reference in their entireties.

The effective daily amount of the compound of formula 1 in the combination with an NMDA receptor antagonist generally will be between about 0.0001 to about 10 mg/kg body weight. The amount of the NMDA receptor antagonist contemplated for use in combination with a compound of formula 1 for treatment of any of the aforementioned disorders, for example Alzheimer's disease, is generally within the range of from about 0.02 mg/kg/day to about 10 mg/kg/day. However, in some instances, the amount of the NMDA antagonist and/or the amount of compound of formula 1 in the combination may be less than would be required on an individual basis to achieve the same desired effect in treating said disorders.

The subject invention also provides for combining a compound of formula 1 with certain substances capable of treating a stroke or traumatic brain injury, such as TPA, NIF, or potassium channel modulators, for example BMS-204352. Such combinations are useful for treating neurodegenerative disorders such as stroke, spinal cord trauma, traumatic brain injury, multiinfarct dementia, epilepsy, pain, Alzheimer's disease, and senile dementia, for example.

For the above-described combination therapies and pharmaceutical compositions, the effective amounts of the compound of the invention and of the other agent can generally be determined by those of ordinary skill in the art, based on the effective amounts for the compounds described herein and those known or described for the other agent known in the art, for example the amounts described in the above-recited patents and patent application incorporated herein. The formulations and routes of administration for such therapies and compositions can be based on the information described herein for compositions and therapies comprising a compound of the invention as the sole active agent and on information provided for the other agent in combination therewith.

A specific compound of formula 1 can be determined to inhibit cdk2, cdk5, or GSK-3 using biological assays known to those of ordinary skill in the art, for example the assays described below.

The specific activity of a compound of formula 1 for inhibition of cdk5 or cdk2 can, for example, be ascertained by means of the following assays using materials available to those of ordinary skill in the art:

Enzyme activities were assayed as the incorporation of [33P] from the gamma phosphate of [33P]ATP (Amersham, cat. no. AH-9968) into biotinylated peptide substrate PKT-PKKAKKL. Reactions were carried out in a buffer containing 50 mM Tris-HCl, pH 8.0; 10 mM MgCl2, 0.1 mM Na3VO4, and 1 mM DTT. The final concentration of ATP was 0.5 uM (final specific radioactivity of 4 uCi/nmol), and the final concentration of substrate was 0.75 uM. Reactions, initiated by the addition of either cdk5 and activator protein p25 or cdk2 and activator cyclin E, were carried out at room temperature for 60 minutes. Reactions were stopped by addition of 0.6 volume of buffer containing (final concentrations): 2.5 mM EDTA, 0.05%Triton-X 100, 100 uM ATP, and 1.25 mg/ml streptavidin coated SPA beads (Amersham cat. no. RPNQ0007). Radioactivity associated with the beads was quantified by scintillation counting.

The specific activity of a compound of formula 1 for inhibition of GSK-3 can be determined in both cell-fee and cell-based assays, both of which are described in the art (see, for example, WO 99/65897). A cell-free assay can be carried out in general by incubating GSK-3 with a peptide substrate, radiolabeled ATP (such as, for example, $\gamma^{33}$P- or $\gamma^{32}$-P-ATP, both available from Amersham, Arlington Heights, Ill.), magnesium ions, and the compound to be assayed. The mixture is incubated for a period of time to allow incorporation of radiolabeled phosphate into the peptide substrate by GSK-3 activity. The reaction mixture is washed to remove unreacted radiolabeled ATP, typically after first transferring all or a portion of the enzyme reaction mixture to a well that contains a uniform amount of a ligand that is capable of binding to the peptide substrate. The amount of $^{33}$P or $^{32}$P remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, derived from the CREB DNA binding protein, described in Wang, et al., *Anal. Biochem.*, 220:397–402 (1994). Purified GSK-3 for an assay may, for example, be obtained from cells transfected with a human GSK-3β expression plasmid as described in, for example Stambolic, et al., *Current Biology* 6:1664–68 (1996).

WO 99/65897; Wang, et al., and Stambolic, et al. are incorporated in their entireties herein by reference.

All of the title compounds of the following Examples had an $IC_{50}$ inhibiting peptide substrate phosphorylation of less than about 50 μM when assayed for cdk5 inhibition according to the preceding assay.

All of the title compounds of the following Examples had an $IC_{50}$ inhibiting peptide substrate phosphorylation of less than about 50 μM when assayed for cdk2 inhibition according to the preceding assay.

All of the title compounds of the following Examples had an $IC_{50}$ for inhibition of GSK-3β of less than about 50 μM.

The following Examples illustrate the present invention. It is to be understood, however, that the invention, as fully described herein and as recited in the claims, is not intended to be limited by the details of the following Examples.

EXAMPLES

Preparation 1

1-(2-Amino-thiazol-5-yl)-cyclobutanol

A solution of 2-aminothiazole (7.1 g, 71 mmol) in THF (360mL) cooled to −78° C. was treated dropwise with n-BuLi (56.18 mL, 142 mmol) while maintaining an internal temperature less than or about equal to −60° C. After addition was completed, the solution was treated dropwise with chlorotrimethylsilane (18 mL, 142 mmol). The reaction solution was warmed to −10° C., then was cooled back to −78° C. n-Butyllithium (28.4 mL, 71 mmol) was added dropwise and after 10 minutes, cyclobutanone (5.33 mL, 71 mmol) was added dropwise. The solution was stirred for 1 hour at −78° C., was quenched with saturated ammonium chloride solution, and was warmed to 23° C. The reaction mixture was extracted with ethyl acetate (300 mL). The organic layer was washed with brine, was dried ($MgSO_4$), was filtered, and solvent was removed in vacuo. The resulting residue was purified by silica gel chromatography (15:1→7:1 $CHCl_3$—MeOH) to afford 7.24 g of 1-(2-amino-thiazol-5-yl)cyclobutanol. $^1$HNMR (400 MHz, DMSO-D6) δ 6.78 (s, 1H), 6.70 (s,2H), 5.58 (s,1H), 22 (m,4H), 1.69 (m, 1H), 1.50 (m,1H).

Preparation 2

5-Cyclobutyl-thiazol-2-ylamine

A solution of 1-(2-amino-thiazol-5-yl)cyclobutanol (Preparation 1; 6.6 g, 39 mmol) in trifluoroacetic acid (150 mL) was treated with 20% palladium hydroxide on carbon (2.3 g). The mixture was evacuated and purged with nitrogen (3 times), then was evacuated and purged with hydrogen gas (50 psi). The mixture was shaken for 24 hours and was evacuated and purged with nitrogen. The mixture was then filtered through Celite which was rinsed with methanol. The organic solvent was removed in vacuo, ethylacetate was added, followed by 29% ammonium hydroxide solution. The aqueous and organic layers were separated and the aqueous layer was extracted with ethylacetate. The combined organic layers were washed with brine, were dried ($MgSO_4$), were filtered, and the solvent was removed in vacuo. The resulting residue was purified by silica gel chromatography (40:1:1 $CHCl_3$—MeOH—$NH_4OH$) to afford 4.75 g of 5-cyclobutyl-thiazol-2-ylamine, the title compound. $^1$HNMR (400 MHz, DMSO-d6): 6.66(s,2H), 6.57(s, 2H), 3.43 (m,1H), 2.20 (m,2H), 1.98–1.7 (m,4H).

Example 1
N-(5-Cyclobutyl-thiazol-2-yl)-2-quinolin-6-yl-acetamide

A solution of 5-cyclobutyl-thiazol-2-ylamine (Preparation 2; 30 mg, 0.195 mmol) was treated with triethylamine (81 µl, 0.585 mmol), 6-quinolylaceticacid (40 mg, 0.214 mmol) and propylphosphonic acid cyclic anhydride ($T_3P$, 126 mL, 0.214 mmol). After 2 hours, an additional 0.2 equiv. of $T_3P$ (22 µl) was added and the reaction was complete by TLC after 15 minutes. The reaction mixture was diluted with $CHCl_3$, was washed with saturated aqu. $NaHCO_3$, and was dried ($MgSO_4$), filtered and concentrated in vacuo. The resulting residue was purified by silica gel chromatography (40:1 $CHCl_3$—MeOH) to afford 55 mg of N-(5-cyclobutyl-thiazol-2-yl)-2-quinolin-6-yl-acetamide, the title compound, as a white solid.

$^1$HNMR (400 MHz; $CDCl_3$) δ 8.88 (dd, J=1.66, 4.15 Hz; 1H), 8.08 (s,1H), 8.06 (s,1H), 7.72 (s,1H), 7.65(m,1H), 7.37 (m,1H), 7.07 (d,J=0.83 Hz,1H), 4.01 (s,2H), 3.62(m,1H), 2.36(m,2H), 2.12(m,2H), 1.97(m,1H), 1.82(m,2H). LRMS m/z (APCl$^+$) 324.0 (M+H)$^+$.

Example 2
(5-Cyclobutyl-thiazol-2-yl)-carbamic acid phenyl ester

A solution of 2-amino-5-cyclobutyl thiazole (Preparation 2; 2.5 g, 1 6 mmol) and diisopropylethylamine (2.82 mL, 16 mmol) in methylene chloride (200 mL) was cooled to −78° C. and phenylchloroformate (2 mL, 16 mmol) was added dropwise. The reaction mixture was slowly warmed to 23° C., was stirred for 1 hour at this temperature, than was washed with aqueous saturated sodium bicarbonate (2 times) and brine (1 time), was dried ($MgSO_4$), was filtered, and was concentrated in vacuo. The resulting white solid was purified by silica gel chromatography (5:1 $CHCl_3$-hexanes) to afford 3.5 g of the title compound as a white solid.

$^1$HNMR (400 MHz, $CDCl_3$): δ 7.42 (m,2H), 7.26 (m,3H), 7.11(s,1H), 3.62(m,1H), 2.37 (m,2H), 2.13 (m,2H), 1.97 (m,1H), 1.89 (m,1H).

Example 3
1-(5-Cyclobutyl-thiazol-2-yl)-3-(2-methyl-quinolin-6-yl)-urea

A solution of (5-cyclobutyl-thiazol-2-yl)-carbamic acid phenyl ester (Example 2; 35 mg, 0.128 mmol) and 6-amino-2-methyl-quinoline (50 mg, 0.128 mmol) in 1,4-dioxane (500 µl) were heated at about 70° C. for 24 hours. Purification by silica gel chromatography (1:3 hexanes-ethylacetate; 40:1→20:1 chloroform-methanol) and subsequent conversion to the HCl salt afforded 40 mg of the title compound. $^1$HNMR (400 MHz, $CDCl_3$) δ 8.11(s,1H), 7.87 (s,7.88,1H), 7.85 (s,1H), 7.45 (d, J=7.6 Hz,1H), 7.16 (d, J=8.4 Hz, 1H), 6.94 (s,1H), 3.55 (m,1 H), 2.67 (s,3H), 2.35 (m,2H), 2.15–1.80 (m,4H). LRMS m/z (APCl$^+$) 339.0 (M+H)$^+$.

Preparation 3
(3-Oxo-cyclobutyl)-carbamic acid benzyl ester

A solution of (3-oxo-cyclobutyl)-carboxylic acid (506 mg, 4.4 mmol) and $Et_3N$(734 µl) in 1:1 THF-Toluene (15 mL) was treated with diphenyl phosphoryl azide (956 µL, 4.4 mmol). The solutions warmed to 60° C. over ca. 45 minutes, at which point nitrogen evolution was noted. After 3 hours, benzyl alcohol (500 µL, 4.8 mmol) was added and the solution was kept at 60° C. for 4 hours. After cooling to room temperature, the solution was diluted with ethylacetate, was washed with saturated aqueous sodium bicarbonate (1 time), 0.5NHCl (2 times) $NaHCO_3$ (1 time), was dried ($MgSO_4$), filtered, and was purified by silica gel chromatography (4:1 Hexanes-Ethylacetate) to afford 405 mg of the title compound. $^1$HNMR(400 MHz, $CDCl_3$) 7.32 (m,5H), 5.44 (s,1H), 5.08(s,2H) 4.29(m,1H), 3.36(m, 2H), 3.06 (m, 2H). LRMS (APCl$^-$) 218.1 (M–H)$^-$.

Preparation 4
[3-(2-Amino-thiazol-5-yl)-3-hydroxy-cyclobutyl]-carbamic acid benzyl ester A solution of 2-aminothiazole (350 mg, 3.5 mmol) in THF (26 mL) at 78° C. was treated dropwise with n-BuLi (2.8 mL, 7 mmol) at such a rate to keep the internal reaction temperature ≦−60° C. The solution was stirred 1 hour, chlorotrimethyl silane was added (888 µL, 7 mmol) (internal temperature ≦−60° C.) and the temperature was increased to −10° C., then was cooled to −78° C. n-BuLi (1.4 mL, 3.5 mmol) was added dropwise (internal temp ≦−60° C.) and after stirring for 10 minutes Preparation 3 (365 mg, 1.67 mmol) in THF (6 mL) was added dropwise. After 1 hour at 78° C., aqueous ammonium chloride was added, the mixture was warmed to 23° C., and was diluted with ethylacetate. The aqueous and organic layers were separated, the organic layer was dried ($MgSO_4$), filtered, and purified by silica gel chromatography (30:1$CHCl_3$—MeOH) to afford 166 mg of the title compound.

Preparation 5
N-[3-(2-Amino-thiazol-5-yl)-cyclobutyl]-acetamide

A solution of Preparation 4 (960 mg,3 mmol) in methylene chloride—Trifluoroacetic acid (1:1, 60 mL) was treated with triethylsilane (1.44 mL, 9 mmol). After 18 hours, more triethylsilane (1 mL,) was added. After 3 hours, solvent was removed in vacuo, methylene chloride was added, followed by a small volume of $NH_4OH$ to neutralize any acid. The mixture was adsorbed onto silica gel and was purified by silica gel chromatography (15:1→10:1 $CHCl_3$—MeOH). 445 mg (49% yield) of )$^+$ [3-(2-amino-thiazol-5-yl) cyclobutyl]-carbamic acid benzyl ester was obtained. LRMS m/z (APCl$^+$) 304 (M+H)$^+$.

A portion of this material (290 mg, 0.96 mmol) was dissolved in trifluoroacetic acid and was treated with anisole (200 µL, 1.9 mmol) and methane sulfonic acid (498 µL, 7.7 mmol) at 0° C.). The solution was allowed to warm to 23° C. over 1 hour, solvent was removed in vacuo, and the residue was then treated with 25% NaOH, solid NaCl, and was extracted with ethylacetate (2 times). The organic layer was dried ($MgSO_4$), filtered, and purified by silica gel chromatography to afford 89 mg of 5-(3-amino-cyclobutyl)-thiazol-2-ylamine. LRMS m/z (APCl$^+$) 170.1 (M+H)$^+$.

A portion of this material (13 mg, 0.077 mmol) was dissolved in $CH_2Cl_2$-methanol (5:1, 6 mL). Triethylamine (32 µL, 0.23 mmol) was added and a solution of acetic anhydride in $CH_2Cl_2$ (0.06M) was added dropwise. Monitoring by TLC (10:1 $CHCl_3$—MeOH, 2% NHClOH) was used to determine when all 5M was consumed. $NH_4OH$ was added, then the reaction mixture was adsorbed onto silica gel and was purified by silica gel chromatography to afford 11 mg of the title compound as a mixture of cis-trans isomers. $^1$HNMR(400 MHz, $CD_3OD$) δ 7.86(s,1H) 6.67 (s,0.25H), 6.60(s,0.75H), 4.4(m,0.25H), 4.2 (m, 0.75H), 3.5 (m, 0.25H) 3.17(m,0.75H), 2.68(m, 2H), 2.37 (m, 1H), 1.98-1.88(m, 4H). LRMS m/z (APCl$^+$) 212.1 (M+H)$^+$.

Preparation 6
2-Bromo-3-Methylpropanal
A solution of 3-methylpropanal (3 g, 35 mmol, 3.7 mL) in dry diethyl ether (50 mL) was treated with 5,5-dibromobarbituric acid (5 g, 17 mmol) and the resulting solution was stirred at 23° C. for 15 hours, during which a precipitate developed. Pentane (30 mL) was added and the precipitate was filtered off. The solution was concentrated in vacuo at 19° C., 350 mmHg, during which a precipitate developed. Pentane (30 mL) was added to the residue and the precipitate was filtered off. The solution was concentrated in vacuo at 19° C., 350 mmHg to afford 3.6 g of the title compound as a volatile oil. $^1$HNMR (400 MHz, $CDCl_3$) δ 9.41 (d,J=3.7 Hz, 1 H), 4.04 (dd, J=6.4, 3.7 Hz, 1H) 1.25 (m, 1H), 1.06(m, 6H).

Example 4
N-[5-(3-Acetylamino-cyclobutyl)-thiazol-2-yl-quinolin-6-yl-acetamide
The procedure to acylate Preparation 5 was the same as that used in Example 1. 10 mg, 0.047 mmol, of Preparation 5 afforded 15 mg of the title compound. $^1$HNMR (400 MHz, $CD_3OD$): δ 8.77(m, 1H), 8.26(m, 1H) 7.96(m, 1H), 7.84(s, 1H), 7.74 (d, J=2.1 Hz, 1H), 7.48 (m, 1H) 7.14 (s, 0.25H) 7.06(s, 0.75H), 4.40(m, 0.25H), 4.20 (m, 0.75H), 3.96 (s, 2H), 2.73 (m, 2H), 2.42 (m, 1H), 1.98(m, 2H), 1.88(s,3H) LRMS m/z (APCl$^+$) 381.0 (M+H)$^+$.

Example 5
(5-Isopropyl-thiazol-2-yl)-(6-methyl-pyridin-2-yl)-amine
A mixture of 2-bromo-3-methyl propanal (Preparation 6, 307 mg, 1.87 mmol) and N-(3-methylpyridyl) thiourea (313 mg, 1.87 mmol) in water (10 mL) was heated at 80° C. for 18 hours. Ammonium hydroxide was added (pH≈11), the mixture was extracted with ethyl acetate and the organic layer was washed with brine, was dried (mgSO$_4$) filtered, and concentrated in vacuo. The resulting residue was purified by preparative thin layer chromatography (1:1 hexanes-ethylacetate) to afford 100 mg (23% yield) of desired product, $^1$HNMR(400 MHz, $CDCl_3$) δ 7.44 (t, J=7.7H, 1H), 7.08(s,1H), 6.67 (m, 2H), 3.12 (m, 1H), 2.52 (s, 3H) 1.34 (d,J=6.85, 6H). LRMS m/z (APCl$^+$) 234.0 (M+H)$^+$.

What is claimed is:
1. A compound of the formula

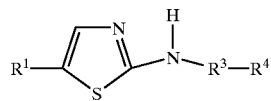

wherein $R^1$ is a straight chain or branched ($C_2$–$C_8$)alkyl, a straight chain or branched ($C_2$–$C_8$)alkenyl, a straight chain or branched ($C_2$–$C_8$)alkynyl, ($C_3$–$C_8$)cycloalkyl, ($C_4$–$C_8$) cycloalkenyl, (3–8 membered) heterocycloalkyl, ($C_5$–$C_{11}$) bicycloalkyl, ($C_7$–$C_{11}$)bicycloalkenyl, (5–11 membered) heterobicycloalkyl, ($C_6$–$C_{14}$) aryl, (5–14 membered) heteroaryl, or ABN–; and wherein $R^1$ is optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)R^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

A and B are each independently selected from straight or branched ($C_1$–$C_8$)alkyl, straight chain or branched ($C_2$–$C_8$)alkenyl, straight chain or branched ($C_2$–$C_8$) alkynyl, ($C_3$–$C_6$)cycloalkyl, ($C_4$–$C_8$)cycloalkenyl, (3–8 membered) heterocycloalkyl, ($C_5$–$C_{11}$) bicycloalkyl, ($C_7$–$C_{11}$)bicycloalkenyl, and (5–11 membered) heterocycloalkyl; or A and B may be connected to form a 3–8 membered heterocyclic ring optionally containing one or two double bonds and optionally containing one or two further hetero atoms selected independently from O, S, and N; and A and B, or the heterocyclic ring formed thereby, can be optionally independently substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

$R^3$ is —$C(=O)NR^9$—, —$C(=O)O$—, —$C(=O)(CR^{10}R^{11})_n$—, or —$(CR^{10}R^{11})_n$—;

$R^4$ is a straight chain or a branched ($C_1$–$C_8$)alkyl, a straight chain or a branched ($C_2$–$C_8$)alkenyl, a straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$) bicycloalkenyl, (5–11 membered) heterobicycloalkyl, ($C_6$–$C_{14}$)aryl, or (5–14 membered) heteroaryl; and wherein $R^4$ is optionally substituted with from one to three substituents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, or $R^7$;

each $R^7$, $R^8$, and $R^9$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^7$, $R^8$, and $R^9$ are each independently optionally substituted with from one to six substituents independently selected from F, Cl, Br, I, $NO_2$, —CN, —$CF_3$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, $OC(=O)R^{10}$, —$OC(=O)OR^{10}$, —$OC(=O)NR^{10}R^{11}$, —$OC(=O)SR^{10}$, —$SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}R^{11}$, and $R^{10}$;

or, when $R^7$ and $R^8$ are as in $NR^7R^8$, they may instead optionally be connected to form with the nitrogen of NR$^7$R$^8$ to which they are attached a heterocycloalkyl moiety of from three to seven ring members, said heterocycloalkyl moiety optionally comprising one or two further heteroatoms independently selected from N, O, and S;

each R$^{10}$, R$^{11}$, and R$^{12}$ is independently selected from H, straight chain or branched (C$_1$–C$_8$)alkyl, straight chain or branched (C$_2$–C$_8$)alkenyl, straight chain or branched (C$_2$–C$_8$ alkynyl), (C$_3$–C$_8$)cycloalkyl, (C$_4$–C$_8$) cycloalkenyl, (3–8 membered) heterocycloalkyl, (C$_5$–C$_{11}$)bicycloalkyl, (C$_7$–C$_{11}$)bicycloalkenyl, (5–11 membered) heterobicycloalkyl, (C$_6$–C$_{14}$)aryl, and (5–14 membered) heteroaryl, wherein R$^{10}$, R$^{11}$, and R$^{12}$ are each independently optionally substituted with from one to six substituents independently selected from F, Cl, Br, I, NO$_2$, —CN, —CF$_3$, —NR$^{13}$R$^{14}$, —NR$^{13}$C(=O)R$^{14}$, —NR$^{13}$C(=O)OR$^{14}$, —NR$^{13}$C(=O)NR$^{14}$R$^{15}$, —NR$^{13}$S(=O)$_2$R$^{14}$, —NR$^{13}$S(=O)$_2$NR$^{14}$R$^{15}$, —OR$^{13}$, —OC(=O)R$^{13}$, —OC(=O)OR$^{13}$, —OC(=O)NR$^{13}$R$^{14}$, —OC(=O)SR$^{13}$, —SR$^{13}$, —S(=O)R$^{13}$, —S(=O)$_2$R$^{13}$, —S(=O)$_2$NR$^{13}$R$^{14}$, —C(=O)R$^{13}$, —C(=O)OR$^{13}$, —C(=O)NR$^{13}$R$^{14}$, and R$^{13}$;

each R$^{13}$, R$^{14}$, and R$^{15}$ is independently selected from H, straight chain or branched (C$_1$–C$_8$)alkyl, straight chain or branched (C$_2$–C$_8$)alkenyl, straight chain or branched (C$_2$–C$_8$ alkynyl), (C$_3$–C$_8$)cycloalkyl, (C$_4$–C$_8$) cycloalkenyl, (3–8 membered) heterocycloalkyl, (C$_5$–C$_{11}$)bicycloalkyl, (C$_7$–C$_{11}$)bicycloalkenyl, (5–11 membered) heterobicycloalkyl, (C$_6$–C$_{14}$)aryl, and (5–14 membered) heteroaryl, wherein R$^{13}$, R$^{14}$, and R$^{15}$ are each independently optionally substituted with from one to six substituents independently selected from F, Cl, Br, I, NO$_2$, —CN, —CF$_3$, —NR$^{16}$R$^{17}$, —NR$^{16}$C(=O)R$^{17}$, —NR$^{16}$C(=O)OR$^{17}$, —NR$^{16}$C(=O)NR$^{17}$R$^{18}$, —NR$^{16}$S(=O)$_2$R$^{17}$, —NR$^{16}$S(=O)$_2$NR$^{17}$R$^{18}$, —OR$^{16}$, —OC(=O)R$^{16}$, —OC(=O)OR$^{16}$, —OC(=O)NR$^{16}$R$^{17}$, —OC(=O)SR$^{16}$, —SR$^{16}$, —S(=O)R$^{16}$, —S(=O)$_2$R$^{16}$, —S(=O)$_2$NR$^{16}$R$^{17}$, —C(=O)R$^{16}$, —C(=O)OR$^{16}$, —C(=O)NR$^{16}$R$^{17}$, and R$^{16}$;

each R$^{16}$, R$^{17}$, and R$^{18}$ is independently selected from H, straight chain or branched (C$_1$–C$_8$)alkyl, straight chain or branched (C$_2$–C$_8$)alkenyl, straight chain or branched (C$_2$–C$_8$ alkynyl), (C$_3$–C$_8$)cycloalkyl, (C$_4$–C$_8$) cycloalkenyl, (3–8 membered) heterocycloalkyl, (C$_5$–C$_{11}$)bicycloalkyl, (C$_7$–C$_{11}$)bicycloalkenyl, (5–11 membered) heterobicycloalkyl, (C$_6$–C$_{14}$)aryl, and (5–14 membered) heteroaryl;

n is 0, 1, 2, or 3;

wherein R$^{10}$ and R$^{11}$ in —C(=O)(CR$^{10}$R$^{11}$)$_n$— and —(CR$^{10}$R$^{11}$)$_n$— are for each iteration of n defined independently as recited above;

or a pharmaceutically acceptable salt thereof.

2. A compound according to claim 1, wherein R$^1$ is cyclobutyl, optionally substituted with from one to six substituents R$^5$.

3. A compound according to claim 2, wherein R$^3$ is —C(=O)(CR$^{10}$R$^{11}$)$_n$—.

4. A compound according to claim 1, wherein R$^1$ is ABN-.

5. A compound according to claim 1, wherein R$^3$ is —(CR$^{10}$R$^{11}$)$_0$— and R$^4$ is (3–8 membered) heterocycloalkyl, (C$_6$–C$_{14}$)aryl, or (5–14 membered) heteroaryl, and R$^4$ is optionally substituted with from one to three substituents R$^6$.

6. A compound according to claim 5, wherein R$^4$ is (C$_6$–C$_{14}$)aryl or (5–14 membered) heteroaryl, each optionally substituted.

7. A compound according to claim 6, wherein R$^4$ is optionally substituted phenyl or optionally substituted pyridyl.

8. A compound according to claim 6, wherein R$^4$ is naphthyl, quinolyl, or isoquinolyl, each optionally substituted.

9. A compound according to claim 6, wherein R$^4$ is unsubstituted napthyl, unsubstituted quinolyl, or unsubstituted isoquinolyl.

10. A compound according to claim 1, wherein R$^3$ is —(CR$^{10}$R$^{11}$)$_0$— and R$^1$ is optionally substituted straight chain or branched (C$_1$–C$_8$)alkyl or optionally substituted straight chain or branched (C$_2$–C$_8$)alkenyl.

11. A compound according to claim 1, wherein R$^3$ is —C(=O)NR$^9$— or —C(=O)(CR$^{10}$R$^{11}$)$_n$—.

12. A compound according to claim 11, wherein R$^{10}$ and R$^{11}$ of —C(=O)(CR$^{10}$R$^{11}$)$_n$— are at each iteration of n both hydrogen and R$^9$ of —C(=O)NR$^9$— is hydrogen.

13. A compound according to claim 1, wherein R$^1$ is optionally substituted (C$_3$–C$_8$)cycloalkyl or optionally substituted (C$_5$–C$_{11}$) bicycloalkyl.

14. A compound according to claim 13, wherein R$^1$ is cyclopropyl, cyclobutyl, cyclopentyl, cyclohexyl, or norbornyl, each optionally substituted.

15. A compound according to claim 13, wherein R$^1$ is (C$_3$–C$_8$)cycloalkyl or optionally substituted (C$_5$–C$_{11}$) bicycloalkyl, and is optionally substituted with from one to three substituents independently selected from F, Cl, Br, I, nitro, cyano, —CF$_3$, —NR$^7$R$^8$, —NR$^7$C(=O)R$^8$, —OR$^7$, —C(=O)OR$^7$, —C(=O)R$^7$, and R$^7$.

16. A compound according to claim 13, wherein R$^1$ is (C$_3$–C$_8$)cycloalkyl or (C$_5$–C$_{11}$)bicycloalkyl, and R$^1$ is substituted with —NR$^7$C(=O)R$^8$, (C$_6$–C$_{14}$)aryl, (3–8 membered) heterocycloalkyl, or (5–14 membered) heteroaryl, and wherein said aryl, heterocycloalkyl, and heteroaryl are each optionally substituted with from one to six substituents independently selected from F, Cl, Br, I, NO$_2$, —CN, —CF$_3$, —NR$^{10}$R$^{11}$, —NR$^{10}$C(=O)R$^{11}$, —NR$^{10}$C(=O)OR$^{11}$, —NR$^{10}$C(=O)NR$^{11}$R$^{12}$, —NR$^{10}$S(=O)$_2$R$^{11}$, —NR$^{10}$S(=O)$_2$NR$^{11}$R$^{12}$, —OR$^{10}$, —OC(=O)R$^{10}$, —OC(=O)OR$^{10}$, —OC(=O)NR$^{10}$R$^{11}$, —OC(=O)SR$^{10}$, —SR$^{10}$, —S(=O)R$^{10}$, —S(=O)$_2$R$^{10}$, —S(=O)$_2$NR$^{10}$R$^{11}$, —C(=O)R$^{10}$, —C(=O)OR$^{10}$, —C(=O)NR$^{10}$R$^{11}$, and R$^{10}$.

17. A compound according to claim 13, wherein R$^1$ is bicyclo-[3.1.0]-hexyl and is optionally substituted.

18. A compound according to claim 1, wherein R$^1$ is optionally substituted straight chain or branched (C$_2$–C$_8$) alkyl or optionally substituted straight chain or branched (C$_2$–C$_8$)alkenyl.

19. A compound according to claim 1, wherein R$^4$ is (C$_6$–C$_{14}$)aryl or (5–14 membered) heteroaryl, each optionally substituted.

20. A compound according to claim 19, wherein R$^4$ is optionally substituted phenyl or optionally substituted pyridyl.

21. A compound according to claim 19, wherein R$^4$ is naphthyl, quinolyl, or isoquinolyl, each optionally substituted.

22. A compound according to claim 19, wherein R$^4$ is napthyl, quinolyl, or isoquinolyl, and is unsubstituted.

23. A compound according to claim 1, selected from the group consisting of:

N-(5-cyclobutyl-thiazol-2-yl)-2-phenyl-acetamide;

N-(5-cyclobutyl-thiazol-2-yl)-isobutyramide;

(5-cyclobutyl-thiazol-2-yl)-carbamic acid phenyl ester;

1-(5-cyclobutyl-thiazol-2-yl)-3-(2,4-dichloro-phenyl)-urea;

1-(5-cyclobutyl-thiazol-2-yl)-3-(2,6-difluoro-phenyl)-urea;
1-(5-cyclobutyl-thiazol-2-yl)-3-(3-trifluoromethyl-phenyl)-urea;
1-(4-chloro-3-trifluoromethyl-phenyl)-3-(5-cyclobutyl-thiazol-2-yl)-urea;
1-(5-cyclobutyl-thiazol-2-yl)-3-(2,4,6-trifluoro-phenyl)-urea;
1-(5-cyclobutyl-thiazol-2-yl)-3-(2,4-difluoro-phenyl)-urea;
1-(5-cyclobutyl-thiazol-2-yl)-3-(2-ethyl-phenyl)-urea;
1-(5-cyclobutyl-thiazol-2-yl)-3-(3-phenoxy-phenyl)-urea;
1-(5-cyclobutyl-thiazol-2-yl)-3-(4-methoxy-phenyl)-urea;
N-(5-cyclobutyl-thiazol-2-yl)-2-(2,4-dichloro-phenyl)-acetamide;
1-(5-cyclobutyl-thiazol-2-yl)-3-phenyl-urea;
1-(4-bromo-3-trifluoromethyl-phenyl)-3-(5-cyclobutyl-thiazol-2-yl)-urea;
1-(5-cyclobutyl-thiazol-2-yl)-3-(1H-indol-5-yl)-urea;
1-(5-cyclobutyl-thiazol-2-yl)-3-(2-methylsulfanyl-phenyl)-urea;
N-(5-cyclobutyl-thiazol-2-yl)-2-(4-methoxy-phenyl)-acetamide;
1-(5-cyclobutyl-thiazol-2-yl)-3-[4-(4-methyl-piperazine-1-sulfonyl)-phenyl]-urea;
1-(5-cyclobutyl-thiazol-2-yl)-3-quinolin-6-yl-urea;
1-(5-cyclobutyl-thiazol-2-yl)-3-(2-methyl-quinolin-6-yl)-urea;
3-{2-[2-(2,4-dichloro-phenyl)-acetylamino]-thiazol-5-yl}-cyclobutanecarboxylic acid butyl ester;
N-(5-cyclobutyl-thiazol-2-yl)-2-pyridin-3-yl-acetamide;
3-{2-[2-(2,4-dichloro-phenyl)-acetylamino]-thiazol-5-yl}-cyclobutanecarboxylic acid;
1-(5-cyclobutyl-thiazol-2-yl)-3-(4-pyridin-3-yl-phenyl)-urea;
1-benzothiazol-5-yl-3-(5-cyclobutyl-thiazol-2-yl)-urea;
N-(5-cyclobutyl-thiazol-2-yl)-2-quinolin-6-yl-acetamide;
1-(3H-benzotriazol-5-yl)-3-(5-cyclobutyl-thiazol-2-yl)-urea;
1-(5-cyclobutyl-thiazol-2-yl)-3-(2-methyl-benzothiazol-5-yl)-urea;
1-biphenyl-3-yl-3-(5-cyclobutyl-thiazol-2-yl)-urea;
1-(3H-benzoimidazol-5-yl)-3-(5-cyclobutyl-thiazol-2-yl)-urea;
1-(5-cyclobutyl-thiazol-2-yl)-3-[4-(2-dimethylamino-ethylamino)-quinolin-6-yl]-urea;
1-(5-cyclobutyl-thiazol-2-yl)-3-[4-(3-hydroxy-propylamino)-quinolin-6-yl]-urea;
(5-cyclobutyl-thiazol-2-yl)-carbamic acid 3-(6-amino-quinolin-4-ylamino)-propyl ester;
N-(5-cyclobutyl-thiazol-2-yl)-2-(2-methyl-benzothiazol-6-yl)-acetamide;
3-hydroxy-pyrrolidine-1-carboxylic acid (5-cyclobutyl-thiazol-2-yl)-amide;
1-(5-cyclobutyl-thiazol-2-yl)-3-[4-(2-hydroxy-cyclohexylamino)-quinolin-6-yl]-urea;
1-(5-cyclobutyl-thiazol-2-yl)-3-quinolin-5-yl-urea;
1-(5-cyclobutyl-thiazol-2-yl)-3-isoquinolin-6-yl-urea;
1-(5-cyclobutyl-thiazol-2-yl)-3-[4-(3-hydroxy-pyrrolidin-1-yl)-quinolin-6-yl]-urea;
1-(5-cyclobutyl-thiazol-2-yl)-3-isoquinolin-5-yl-urea;
2-(1H-benzoimidazol-5-yl)-N-(5-cyclobutyl-thiazol-2-yl)-acetamide;
N-(5-cyclobutyl-thiazol-2-yl)-2-(5,6-dimethyl-benzoimidazol-1-yl)-acetamide;
1-(5-cyclobutyl-thiazol-2-yl)-3-[4-(2-hydroxy-cyclopentylamino)-quinolin-6-yl]-urea;
N-(5-cyclobutyl-thiazol-2-yl)-2-indol-1-yl-acetamide;
1-(3H-benzoimidazol-4-yl)-3-(5-cyclobutyl-thiazol-2-yl)-urea;
N-(5-cyclobutyl-thiazol-2-yl)-2-(1H-indol-3-yl)-acetamide;
N-(5-cyclobutyl-thiazol-2-yl)-2-quinolin-5-yl-acetamide;
1-(5-cyclobutyl-thiazol-2-yl)-3-(1H-indazol-6-yl)-urea;
1-(5-cyclobutyl-thiazol-2-yl)-3-(4-methyl-2-oxo-1,2-dihydro-quinolin-7-yl)-urea;
1-(5-cyclobutyl-thiazol-2-yl)-3-[2-(4-nitro-phenyl)-1H-benzoimidazol-5-yl]-urea;
1-benzo[1,3]dioxol-5-yl-3-(5-cyclobutyl-thiazol-2-yl)-urea;
1-(5-cyclobutyl-thiazol-2-yl)-3-(4-methoxymethyl-2-oxo-2H-chromen-7-yl)-urea;
1-(5-cyclobutyl-thiazol-2-yl)-3-(4-methyl-2-oxo-2H-chromen-7-yl)-urea;
1-(5-cyclobutyl-thiazol-2-yl)-3-(2-oxo-2,3-dihydro-1H-benzoimidazol-5-yl)-urea;
1-(1-acetyl-2,3-dihydro-1H-indol-6-yl)-3-(5-cyclobutyl-thiazol-2-yl)-urea;
1-(5-cyclobutyl-thiazol-2-yl)-3-(4,7-dimethoxy-3H-benzoimidazol-5-yl)-urea;
1-(5-cyclobutyl-thiazol-2-yl)-3-(2-pyridin-2-yl-1H-benzoimidazol-5-yl)-urea;
1-(5-cyclobutyl-thiazol-2-yl)-3-[2-(1,1,2,2,3,3,3-heptafluoro-propyl)-1H-benzoimidazol-5-yl]-urea;
1-(5-cyclobutyl-thiazol-2-yl)-3-(6-fluoro-3-prop-2-ynyl-2-trifluoromethyl-3H-benzoimidazol-5-yl)-urea;
1-(5-cyclobutyl-thiazol-2-yl)-3-(1-ethyl-2-methyl-1H-benzoimidazol-5-yl)-urea;
1-(5-cyclobutyl-thiazol-2-yl)-3-(1H-indol-6-yl)-urea;
1-(5-cyclobutyl-thiazol-2-yl)-3-(2-methyl-1H-benzoimidazol-5-yl)-urea;
5-[3-(5-cyclobutyl-thiazol-2-yl)-ureido]-1H-indole-2-carboxylic acid ethyl ester;
1-benzo[1,2,3]thiadiazol-4-yl-3-(5-cyclobutyl-thiazol-2-yl)-urea;
1-(5-cyclobutyl-thiazol-2-yl)-3-(1,4-dioxo-1,2,3,4-tetrahydro-phthalazin-5-yl)-urea;
1-(5-cyclobutyl-thiazol-2-yl)-3-(1H-indazol-7-yl)-urea;
1-(5-cyclobutyl-thiazol-2-yl)-3-(1H-indol-4-yl)-urea;
1-(5-cyclobutyl-thiazol-2-yl)-3-(2-oxo-2,3-dihydro-1H-benzoimidazol-4-yl)-urea;
1-benzooxazol-4-yl-3-(5-cyclobutyl-thiazol-2-yl)-urea;
N-(5-cyclobutyl-thiazol-2-yl)-2-(2-methyl-3H-benzoimidazol-5-yl)-acetamide;
1-(5-cyclobutyl-thiazol-2-yl)-3-quinolin-8-yl-urea;
1-(5-cyclobutyl-thiazol-2-yl)-3-isoquinolin-8-yl-urea;
1-(3H-benzotriazol-4-yl)-3-(5-cyclobutyl-thiazol-2-yl)-urea;
N-(5-cyclobutyl-thiazol-2-yl)-2-isoquinolin-5-yl-acetamide;
N-(5-cyclobutyl-thiazol-2-yl)-2-quinolin-6-yl-acetamide;

1-(5-cyclobutyl-thiazol-2-yl)-3-isoquinolin-5-yl-urea;
N-[5-(3-acetylamino-cyclobutyl)-thiazol-2-yl]-2-quinolin-6-yl-acetamide;
N-(5-cyclobutyl-thiazol-2-yl)-2-(4-nitro-phenyl)-acetamide;
2-(4-amino-phenyl)-N-(5-cyclobutyl-thiazol-2-yl)-acetamide;
2-(4-acetylamino-phenyl)-N-(5-cyclobutyl-thiazol-2-yl)-acetamide;
N-(5-cyclobutyl-thiazol-2-yl)-2-[4-(2-pyridin-3-yl-acetylamino)-phenyl]-acetamide;
N-(5-cyclobutyl-thiazol-2-yl)-2-[4-(2-morpholin-4-yl-ethylamino)-phenyl]-acetamide;
(5-isopropyl-thiazol-2-yl)-pyridin-2-yl-amine;
(3-chloro-5-trifluoromethyl-pyridin-2-yl)-(5-isopropyl-thiazol-2-yl)-amine;
(5-isopropyl-thiazol-2-yl)-phenyl-amine;
(5-chloro-pyridin-2-yl)-(5-isopropyl-thiazol-2-yl)-amine;
(5-isopropyl-thiazol-2-yl)-(6-methyl-pyridin-2-yl)-amine;
(5-isopropyl-thiazol-2-yl)-(5-methyl-pyridin-2-yl)-amine;
(5-isopropyl-thiazol-2-yl)-(4-methyl-pyridin-2-yl)-amine;
(2-chloro-pyridin-4-yl)-(5-isopropyl-thiazol-2-yl)-amine; and
N-(5-dimethylamino-thiazol-2-yl)-2-phenyl-acetamide;
and pharmaceutically acceptable salts of the foregoing compounds.

24. A compound of the formula

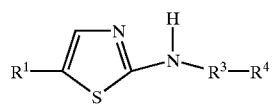

wherein $R^1$ is a straight chain or branched ($C_2$–$C_8$) alkenyl, a straight chain or branched ($C_2$–$C_8$)alkynyl, ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$) aryl, (5–14 membered) heteroaryl, or ABN–; and wherein $R^1$ is optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^7R^8$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

A and B are each independently selected from straight or branched ($C_1$–$C_8$)alkyl, straight chain or branched ($C_2$–$C_8$)alkenyl, straight chain or branched ($C_2$–$C_8$) alkynyl, ($C_3$–$C_6$)cycloalkyl, ($C_4$–$C_8$)cycloalkenyl, (3–8 membered) heterocycloalkyl, ($C_5$–$C_{11}$) bicycloalkyl, ($C_7$–$C_{11}$)bicycloalkenyl, and (5–11 membered) heterocycloalkyl; or A and B may be connected to form a 3–8 membered heterocyclic ring optionally containing one or two double bonds and optionally containing one or two further hetero atoms selected independently from O, S, and N; and A and B, or the heterocyclic ring formed thereby, can be optionally independently substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, and $R^7$;

$R^3$ is —$C(=O)NR^9$—, —$C(=O)O$—, —$C(=O)(CR^{10}OR^{11})_n$—, or —$(CR^{10}R^{11})_n$—;

$R^4$ is a straight chain or a branched ($C_1$–$C_8$)alkyl, a straight chain or a branched ($C_2$–$C_8$)alkenyl, a straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$) bicycloalkenyl, (5–11 membered) heterobicycloalkyl, ($C_6$–$C_{14}$)aryl, or (5–14 membered) heteroaryl; and wherein $R^4$ is optionally substituted with from one to three substituents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, or $R^7$;

each $R^7$, $R^8$, and $R^9$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^7$, $R^8$, and $R^9$ are each independently optionally substituted with from one to six substituents independently selected from F, Cl, Br, I, $NO_2$, —CN, —$CF_3$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, $OC(=O)R^{10}$, —$OC(=O)OR^{10}$, —$OC(=O)NR^{10}OR^{11}$, —$OC(=O)SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}OR^{11}$, and $R^{10}$;

or, when $R^7$ and $R^8$ are as in $NR^7R^8$, they may instead optionally be connected to form with the nitrogen of $NR^7R^8$ to which they are attached a heterocycloalkyl moiety of from three to seven ring members, said heterocycloalkyl moiety optionally comprising one or two further heteroatoms independently selected from N, O, and S;

each $R^{10}$, $R^{11}$, and $R^{12}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{10}$, $R^{11}$, and $R^{12}$ are each independently optionally substituted with from one to six substituents independently selected from F, Cl, Br, I, $NO_2$, —CN, —$CF_3$, —$NR^{13}R^{14}$, —$NR^{13}C(=O)R^{14}$, —$NR^{13}C(=O)OR^{14}$, —$NR^{13}C(=O)NR^{14}R^{15}$, —$NR^{13}S(=O)_2R^{14}$, —$NR^{13}S(=O)$ $_2NR^{14}R^{15}$, —$OR^{13}$, —$OC(=O)R^{13}$, —$OC(=O)OR^{13}$, —$OC(=O)NR^{13}R^{14}$, —$OC(=O)SR^{13}$, —$SR^{13}$, —$S(=O)R^{13}$, —$S(=O)_2R^{13}$, —$S(=O)_2NR^{13}R^{14}$, —$C(=O)R^{13}$, —$C(=O)OR^{13}$, —$C(=O)NR^{13}R^{14}$, and $R^{13}$;

each $R^{13}$, $R^{14}$, and $R^{15}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{13}$, $R^{14}$, and $R^{15}$ are each independently optionally substituted with from one to six substituents independently selected from F, Cl, Br, I, $NO_2$, —CN, —$CF_3$, —$NR^{16}R^{17}$, —$NR^{16}C(=O)R^{17}$, —$NR^{16}C(=O)OR^{17}$, —$NR^{16}C(=O)NR^{17}R^{18}$, —$NR^{16}S(=O)_2R^{17}$, —$NR^{16}S(=O)_2NR^{17}R^{18}$, —$OR^{16}$, —$OC(=O)R^{16}$, —$OC(=O)OR^{16}$, —$OC(=O)NR^{16}R^{17}$, —$OC(=O)SR^{16}$, —$SR^{16}$, —$S(=O)R^{16}$, —$S(=O)_2R^{16}$, —$S(=O)_2NR^{16}R^{17}$, —$C(=O)R^{16}$, —$C(=O)OR^{16}$, —$C(=O)NR^{16}R^{17}$, and $R^{16}$;

each $R^{16}$, $R^{17}$, and $R^{18}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$) cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl;

n is 0, 1, 2, or 3;

wherein $R^{10}$ and $R^{11}$ in —$C(=O)(CR^{10}R^{11})_n$— and —$(CR^{10}R^{11})_n$— are for each iteration of n defined independently as recited above;

or a pharmaceutically acceptable salt thereof.

\* \* \* \* \*